US010434169B2

(12) United States Patent
Kirn et al.

(10) Patent No.: US 10,434,169 B2
(45) Date of Patent: Oct. 8, 2019

(54) GENERATION OF ANTIBODIES TO TUMOR ANTIGENS AND GENERATION OF TUMOR SPECIFIC COMPLEMENT DEPENDENT CYTOTOXICITY BY ADMINISTRATION OF ONCOLYTIC VACCINIA VIRUS

(71) Applicants: SILLAJEN BIOTHERAPEUTICS, INC., San Francisco, CA (US); SILLAJEN, INC., Busan (KR)

(72) Inventors: David Kirn, Mill Valley, CA (US); John Bell, Ottawa (CA); Caroline Breitbach, San Francisco, CA (US); Anne Moon, San Francisco, CA (US); Tae-Ho Hwang, Busan (KR); Yu Kyoung Lee, Busan (KR); Mi-kyung Kim, Busan (KR)

(73) Assignees: SILLAJEN, INC, Busan (KR); SILLAJEN BIOTHERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 15/892,247

(22) Filed: Feb. 8, 2018

(65) Prior Publication Data
US 2018/0214538 A1  Aug. 2, 2018

Related U.S. Application Data

(62) Division of application No. 13/978,113, filed as application No. PCT/US2012/020173 on Jan. 4, 2012, now Pat. No. 9,919,047.

(60) Provisional application No. 61/429,622, filed on Jan. 4, 2011.

(51) Int. Cl.
| | | |
|---|---|---|
| A61K 39/285 | (2006.01) | |
| A61K 39/00 | (2006.01) | |
| C07K 16/30 | (2006.01) | |
| A61K 35/76 | (2015.01) | |
| A61K 35/761 | (2015.01) | |
| A61K 35/763 | (2015.01) | |
| A61K 35/768 | (2015.01) | |
| A61K 35/26 | (2015.01) | |
| A61K 39/12 | (2006.01) | |
| A61K 39/125 | (2006.01) | |
| A61K 39/145 | (2006.01) | |
| A61K 39/165 | (2006.01) | |
| A61K 39/17 | (2006.01) | |
| A61K 39/205 | (2006.01) | |
| A61K 39/235 | (2006.01) | |
| A61K 39/245 | (2006.01) | |
| A61K 39/395 | (2006.01) | |
| A61K 45/06 | (2006.01) | |
| C07K 16/18 | (2006.01) | |
| C12N 7/00 | (2006.01) | |
| G01N 33/574 | (2006.01) | |

(52) U.S. Cl.
CPC ............ *A61K 39/285* (2013.01); *A61K 35/26* (2013.01); *A61K 35/76* (2013.01); *A61K 35/761* (2013.01); *A61K 35/763* (2013.01); *A61K 35/768* (2013.01); *A61K 39/0011* (2013.01); *A61K 39/12* (2013.01); *A61K 39/125* (2013.01); *A61K 39/145* (2013.01); *A61K 39/165* (2013.01); *A61K 39/17* (2013.01); *A61K 39/205* (2013.01); *A61K 39/235* (2013.01); *A61K 39/245* (2013.01); *A61K 39/395* (2013.01); *A61K 45/06* (2013.01); *C07K 16/18* (2013.01); *C07K 16/30* (2013.01); *C12N 7/00* (2013.01); *G01N 33/574* (2013.01); *A61K 2039/505* (2013.01); *A61K 2039/507* (2013.01); *A61K 2039/55522* (2013.01); *C07K 2317/14* (2013.01); *C07K 2317/734* (2013.01); *C12N 2710/10034* (2013.01); *C12N 2710/16632* (2013.01); *C12N 2710/16634* (2013.01); *C12N 2710/24034* (2013.01); *C12N 2710/24132* (2013.01); *C12N 2720/12232* (2013.01); *C12N 2750/14034* (2013.01); *C12N 2760/16034* (2013.01); *C12N 2760/18134* (2013.01); *C12N 2760/18434* (2013.01); *C12N 2760/18734* (2013.01); *C12N 2760/20034* (2013.01); *C12N 2760/20232* (2013.01); *C12N 2770/32034* (2013.01); *C12N 2770/32334* (2013.01); *C12N 2770/36034* (2013.01)

(58) Field of Classification Search
None
See application file for complete search history.

(56) References Cited

FOREIGN PATENT DOCUMENTS

| | | |
|---|---|---|
| JP | 2002-529707 A | 9/2002 |
| JP | 2005-508616 A | 4/2005 |
| WO | 2004/018680 A1 | 3/2004 |

OTHER PUBLICATIONS

Park et al (Lancet Oncol, 2008, 9: 533-542).*
Shebzukhov et al (Immunology Letters, 2005, 100: 88-93).*
Kim et al (Sci Transl Med, 2013, 5(185): 1-10).*

* cited by examiner

*Primary Examiner* — Sean E Aeder
(74) *Attorney, Agent, or Firm* — Christopher M. Cabral; Polsinelli PC

(57) ABSTRACT

The present invention relates to methods and compositions for use in inducing tumor-specific antibody mediated complement-dependent cytotoxic response in an animal having a tumor comprising administering to said animal a composition comprising a replication competent oncolytic virus wherein administration of the composition induces in the animal production of antibodies that mediate a CDC response specific to said tumor.

13 Claims, 26 Drawing Sheets

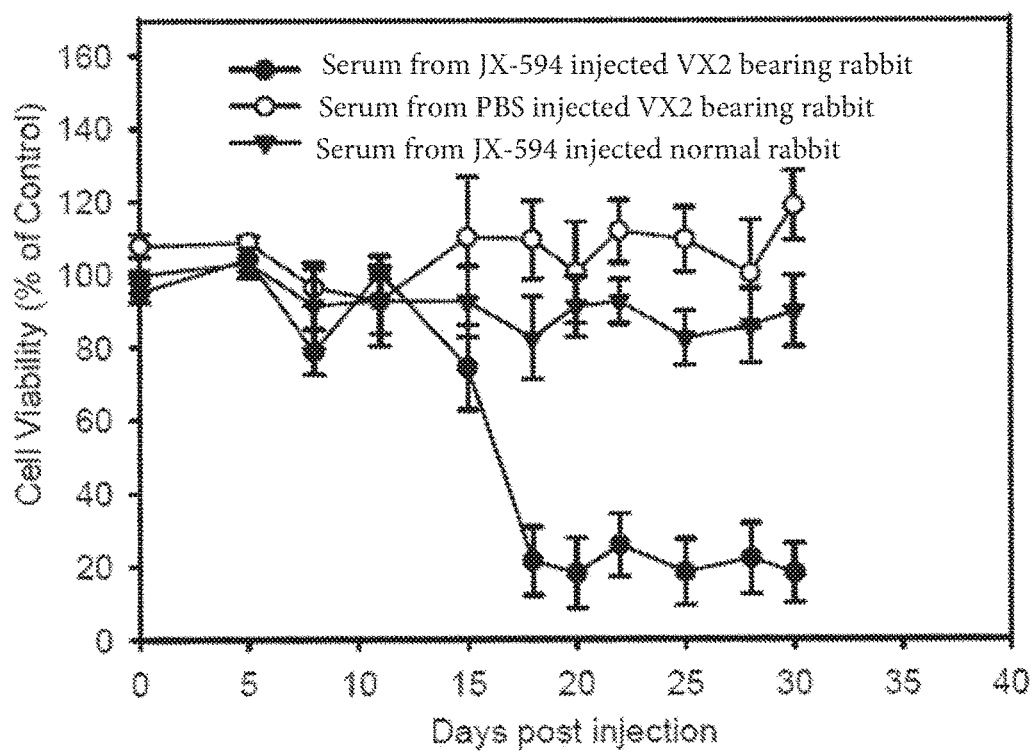

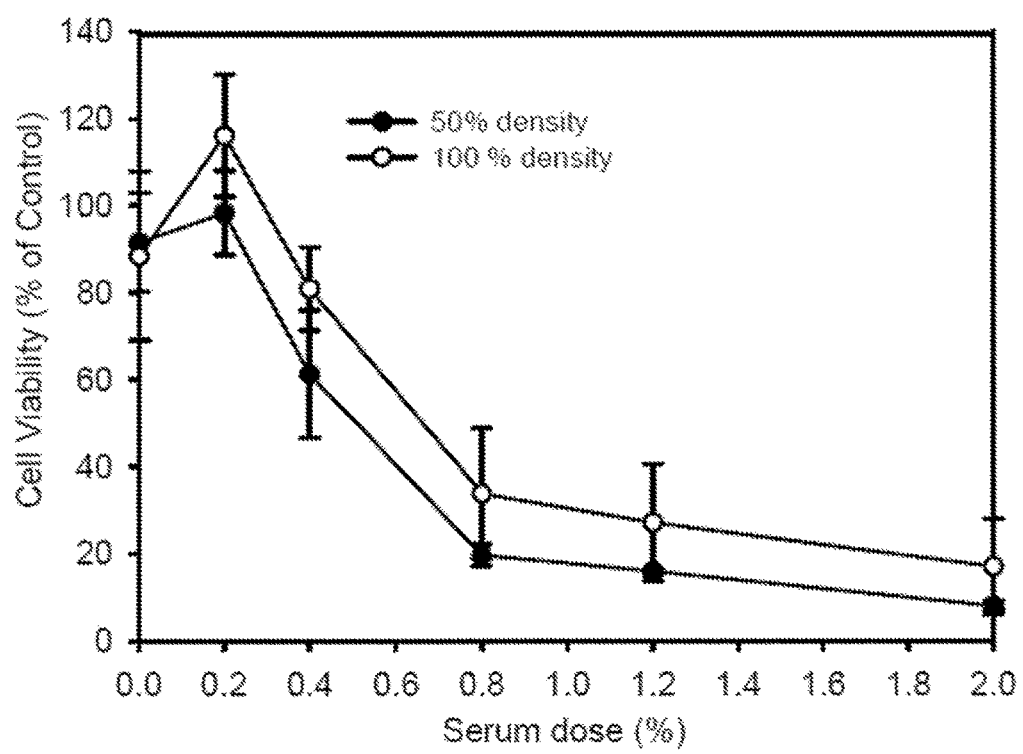

FIGURE 2A
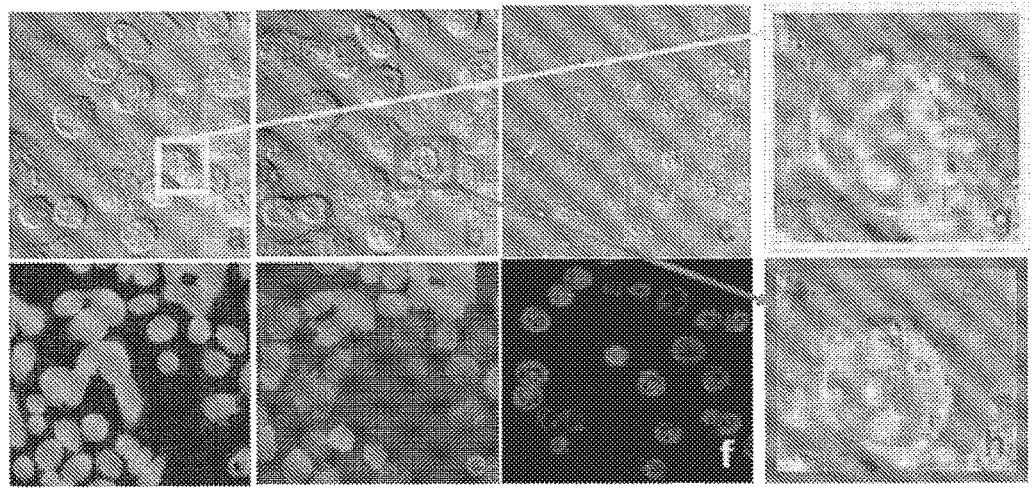
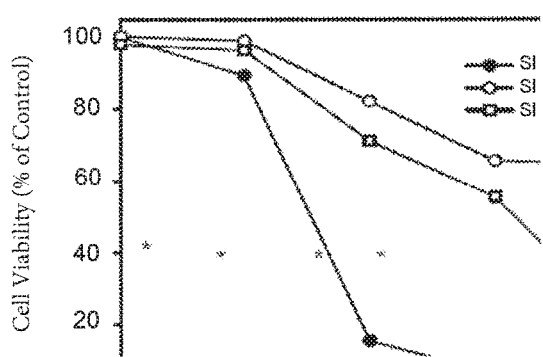
Figure 2B
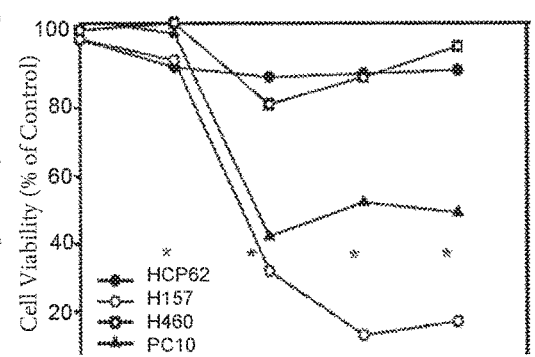
Figure 2C

"b" serum    "c" serum    "d" serum

1702-HCC pt.

1705-HCC pt.

103 patient – Lung Ca.

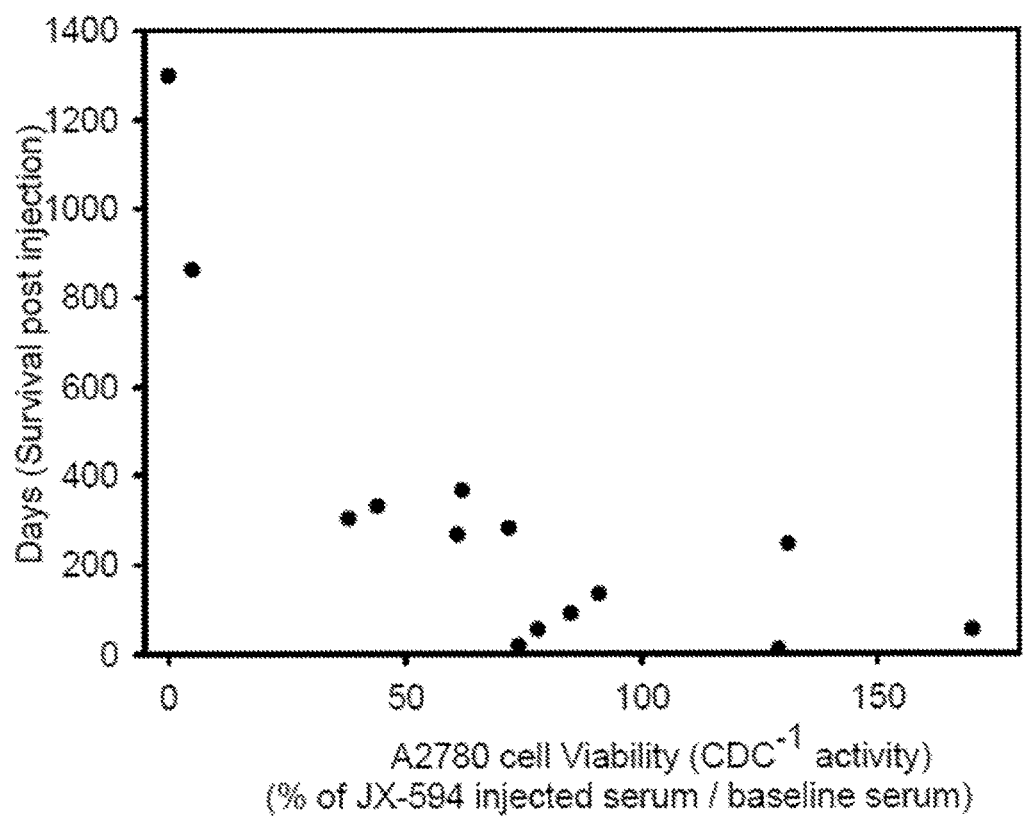

GENERATION OF ANTIBODIES TO TUMOR ANTIGENS AND GENERATION OF TUMOR SPECIFIC COMPLEMENT DEPENDENT CYTOTOXICITY BY ADMINISTRATION OF ONCOLYTIC VACCINIA VIRUS

RELATED APPLICATIONS

The present application is a divisional application of U.S. application Ser. No. 13/978,113 which is the 35 USC 371 U.S. national stage of international application no. PCT/US2012/020173, filed on Jan. 4, 2012 and claims the benefit of priority of U.S. Provisional Application No. 61/429,622, which was filed on Jan. 4, 2011, each of which is incorporated herein by reference in its entirety.

FEDERALLY SPONSORED RESEARCH OR DEVELOPMENT

This invention was made with Korean government support under Grant No. A060001 awarded by Ministry for Health, Welfare, and Family Affairs, Republic of Korea Korean Health technology R&D project entitled "Study on Oncolytic Virus; translational research and clinical application," host organization Pusan National University period of study from March 2001-June 2009.

FIELD OF THE INVENTION

The present invention relates to new mechanisms of action for intervention of cancer therapy and methods and compositions devised for cancer therapies relying on such new mechanisms of action.

BACKGROUND OF THE INVENTION

New cancer therapies with novel mechanisms-of-action (MOA) are needed. Current therapies often have limited efficacy when used as single agents, so in practice are used in combination for maximal effect. Novel agents should ideally lack cross-resistance with approved therapies, and should have multiple complementary MOA[1-4]. Engineered viruses have been developed for cancer treatment using different approaches, including "gene therapy" (therapeutic transgene transfer in a replication-incompetent virus)[5-7] and cancer vaccines (expression of tumor antigens, co-stimulatory molecules and/or cytokines)[8-10]. However, gene therapy has failed to date in patients due to inefficient delivery to sufficient numbers of cancer cells locally and systemically. In contrast, virus-based cancer vaccines have been limited by tumor immune evasion and exclusive reliance on host factors for efficacy in patients with advanced bulky cancers. Immune evasion is most likely with vaccine approaches that rely on the expression of a single tumor antigen and/or a single cytokine. Broad-based therapeutic cancer vaccines are needed to express multiple tumor antigens, cytokines, immune cell recruitment and activation, and immune response danger signals.

In contrast, oncolytic viruses were developed to take advantage of viruses' natural ability to infect, multiply within and subsequently lyse cancer cells[11-14]. First-generation oncolytic viruses were inherently cancer-selective (e.g. reovirus[15-16], VSV[17-18]) whereas second-generation agents were engineered for cancer selectivity (e.g. adenovirus[19-20] and herpes simplex virus[21-22] deletion mutants). Clinical trial data with these agents demonstrated safety and cancer selectivity, but therapeutic potency was limited both after direct intratumoral or intravenous injection[23]; systemic spread and/or reproducible delivery to distant tumors were limited, however. Systemic anti-cancer potency and blood-borne delivery to metastatic tumors therefore had to be improved.

Given both the potential and the limitations with each of these three individual virus-based approaches, we asked whether it was possible to combine and optimize the best attributes of each into a single therapeutic agent. Targeted and armed oncolytic poxviruses have the potential to do so. JX-594 is a $3^{rd}$-generation oncolytic poxvirus therapeutic designed to have three complementary MOA including: 1) direct replication-mediated oncolysis, and 2) active cancer vaccination. JX-594 is a Wyeth vaccinia virus vaccine-derived oncolytic with disruption of the viral thymidine kinase gene and expression of the human granulocyte-monocyte colony stimulating factor (hGM-CSF) and β-galactosidase transgenes under control of the synthetic early-late and p7.5 promoters, respectively[24]. Vaccinia was used as the virus backbone because of its stability in blood for blood-borne delivery to tumors[25]. JX-594 is designed to induce cancer vaccination through simultaneous cancer cell lysis and endogenous tumor antigen release, expression of hGM-CSF to support antigen-presenting cell activation, recruitment of immune effector cells and proinflammatory cytokine induction. Clearance of vaccinia itself is primarily via infected cell clearance through cell-mediated immune mechanisms.

The inventors have now discovered a new method of treatment of cancer using oncolytic viruses to address the need in the art for new cancer therapies.

BRIEF SUMMARY OF THE INVENTION

The present invention relates to methods and compositions for use in inducing tumor-specific antibody mediated complement-dependent cytotoxic response in an animal having a tumor comprising administering to the animal a composition comprising a replication competent oncolytic virus wherein administration of the composition induces in the animal production of antibodies that mediate a CDC response specific to the tumor.

In specific embodiments, the invention provides methods of inducing tumor-specific antibody mediated complement-dependent cytotoxic response in an animal having a tumor comprising administering to the animal a composition comprising a replication competent oncolytic virus wherein administration of the composition induces antibodies in the animal that mediate a CDC response specific to the tumor. More particularly, the administration of the oncolytic virus does not induce CDC response in an animal that does not have a tumor.

The oncolytic virus may be any oncolytic virus. Exemplary such viruses may be selected from the group consisting of a poxvirus, adenovirus, adeno-associated virus, herpes simplex virus, Newcastle disease virus, vesicular stomatitis virus, mumps virus, influenza virus, Parvovirus, measles virus, human hanta virus, myxoma virus, cytomegalovirus (CMV), lentivirus, Coxsackievirus, Echoviruses, Seneca Valley Virus and Sindbis virus. In specific embodiments, the oncolytic virus is an oncolytic poxvirus. Specific examples of oncolytic viruses that may be used include for example mutated vaccinia virus expressing GM-CSF, p53 expressing viruses, vesicular stomatitis virus (VSV), ONYX-15, Delta24, adenoviruses mutated in the VA1 region, vaccinia viruses mutated in the K3L or E3L region, Telomelysin, Telomelysin-GFP, parapoxvirus orf viruses mutated in the OV20.0L gene, Genelux virus, and herpes viruses mutated in the gamma (1)34.5 gene. In a specific exemplary embodiment, the oncolytic poxvirus is JX-594. The oncolytic virus may comprise therapeutic or other transgene. For example, the transgene may be a heterologous nucleic acid sequence encodes GM-CSF, or other cytokine, chemokine, marker and/or imaging gene, suicide gene, prodrug enzyme genes carboxyl esterase and cytosine deaminase, tumor suppressor gene and the like.

The tumor against which the antibodies are raised may be any tumor including but not limited to a tumor selected from the group consisting of astrocytoma, oligodendroglioma, meningioma, neurofibroma, glioblastoma, ependymoma, Schwannoma, neurofibrosarcoma, neuroblastoma, pituitary adenoma, medulloblastoma, head and neck cancer, melanoma, prostate carcinoma, renal cell carcinoma, pancreatic cancer, breast cancer, lung cancer, colon cancer, gastric cancer, bladder cancer, liver cancer, bone cancer, rectal cancer, ovarian cancer, sarcoma, gastric cancer, esophageal cancer, cervical cancer, fibrosarcoma, squamous cell carcinoma, neurectodermal, thyroid tumor, Hodgkin's lymphoma, non-Hodgkin's lymphoma, hepatoma, mesothelioma, epidermoid carcinoma, and tumorigenic diseases of the blood.

Also included is a method of generating in vivo antibodies that mediate an anti-tumor CDC response comprising administering to a subject a composition comprising a replication competent oncolytic virus wherein administration of the composition induces antibodies that mediate a CDC response specific to the tumor. The method may further comprise harvesting blood from the subject after the administration and isolating CDC-response producing antibodies from the blood.

Also contemplated is a composition comprising CDC-response producing antibodies isolated from the blood of a subject that has been treated with a replication competent oncolytic virus in an amount and manner effective to induce antibodies that mediate a CDC response specific to a tumor. In specific embodiments, the composition is serum collected from the subject.

Also contemplated is a method of inhibiting the growth of or killing a cancer cell comprising contacting the cancer cell with a composition of the invention. In specific embodiments, the contacting comprises contacting cancer cells in vitro with the composition. In other embodiments, the contacting comprises infusing a subject having cancer with a composition comprising harvested antibodies, harvested B cells, antibodies produced by the harvested B cells or a combination thereof. In the treatment methods of the invention, the cancer cell may be in vivo in a subject and the contacting comprising administering a medicament comprising the composition. In additional embodiments, the treatment methods may further comprise administering to the subject a further anti-cancer therapeutic agent.

The invention further comprises methods of treating a cancer subject comprising administering to the subject composition comprising a composition of the invention that comprises CDC-response producing antibodies isolated from the blood of a subject that has been treated with a replication competent oncolytic virus in an amount and manner effective to induce antibodies that mediate a CDC response specific to a tumor. In some embodiments, the composition is autologous to the patient and is isolated from the cancer patient and reinfused into the cancer patient. In other embodiments, the composition is heterologous to the cancer patient is isolated from a cancer patient that is different from the cancer patient being treated with the composition. In either case, the subject may be treated with a further anticancer therapeutic agent.

In the treatment methods of the invention the cancer subject may have a solid tumor and the composition is administered intratumorally, intravenously, intraperitoneally or a combination thereof. In specific embodiments, the cancer subject has a solid tumor that is resected prior to, concurrently or subsequent to administering the composition of the invention. In some embodiments, the cancer subject has a solid tumor and the composition reduces the size of the tumor. In other embodiments, the cancer subject has a solid tumor and the administration reduces metastatic spread of the solid tumor. In the treatment methods, the cancer may be selected from the group consisting of astrocytoma, oligodendroglioma, meningioma, neurofibroma, glioblastoma, ependymoma, Schwannoma, neurofibrosarcoma, neuroblastoma, pituitary adenoma, medulloblastoma, head and neck cancer, melanoma, prostate carcinoma, renal cell carcinoma, pancreatic cancer, breast cancer, lung cancer, colon cancer, gastric cancer, bladder cancer, liver cancer, bone cancer, rectal cancer, ovarian cancer, sarcoma, gastric cancer, esophageal cancer, cervical cancer, fibrosarcoma, squamous cell carcinoma, neurectodermal, thyroid tumor, Hodgkin's lymphoma, non-Hodgkin's lymphoma, hepatoma, mesothelioma, epidermoid carcinoma, and tumorigenic diseases of the blood.

The invention also provides a teaching of methods of tailoring a cancer therapy for a subject having cancer comprising:
a) administering to the subject a composition comprising a replication competent oncolytic virus wherein administration of the composition induces in the subject production of antibodies that mediate a CDC response specific to the cancer in the subject;
b) isolating blood from the subject wherein the blood comprises harvested antibodies, harvested B cells against the cancer;
c) expanding or isolating the antibodies or producing antibodies from the B cells; to produce an immunotherapy composition specific for the subject and
d) administering the subject with the immunotherapy composition of step (c). In such methods, the immunotherapy composition may be administered in immediately upon isolation of the antibodies. Alternatively, the immunotherapy composition is stored for further therapeutic treatment of the subject.

A further aspect of the invention relates to a method of identifying a tumor-specific antigen comprising cloning a cDNA library prepared from a cancer cell into an expression vector; performing a primary immunoscreen by contacting the expression vector with serum from a subject that has been treated with that has been treated with a replication competent oncolytic virus in an amount and manner effective to induce antibodies that mediate a CDC response specific to a tumor wherein the serum is isolated from the subject after administration of the oncolytic virus and generation of the CDC specific response; and isolating antigens from the cDNA library that are recognized by the serum.

BRIEF DESCRIPTION OF SEVERAL VIEWS OF THE DRAWINGS

For a more complete understanding of the present invention, reference is now made to the following descriptions taken in conjunction with the following accompanying drawings.

FIGS. 1A-D: Serum effect of JX-594 injected into VX2 tumor bearing rabbit. Serum was collected at baseline, 3 weeks and 6 weeks post JX-594 or PBS treatment. VX2 was isolated from VX2 tissues enzymatically and maintained in vitro with Dulbecco's modified Eagle's medium (DMEM) with 10% FBS for 8 passages. FIG. 1A, Death of isolated VX2 tumor cell but not of rabbit PBMC by JX-594 injected but not by PBS injected serum into VX2 bearing but not into normal rabbit. 3% Serum obtained from JX-594 injected into (normal vs. VX2 bearing rabbit) or PBS injected VX2 bearing rabbit were treated (each animal (n=3 for each condition, triplicates from each serum sample meaning reaction No.=9 for each) in isolated VX2 cells or rabbit PBMC. FIG. 1B, Time dependent antitumoral effect of serum against isolated VX2 cells after JX-594 injection into VX2 bearing rabbit. JX-594 ($10^9$ pfu for each rabbit) was injected at day 0 and day 7 and serum was serially obtained at each point. FIG. 1C, Dose dependent antitumoral effect of serum against isolated VX2 cells after JX-594 injection into VX2 bearing rabbit. FIG. 1D, Western blotting of JX-594 injected serum.

FIG. 2A. Representative confocal microscopy of human RCC SNU349 cell line after treatment of JX-594 injected human serum (at day 92 after four cycle JX-594 injection into #301 renal cellular carcinoma patient). a, d—before serum (5%) addition; b, e—10 min later after serum (5%) addition, c, f—30 min later after serum (5%) addition (no fluorescence at 30 min, not displayed); g—magnified of yellow area in a, h—magnified view of red area in b (please note cell lysis via Membrane attack formation (MAF) which is typical of CDC effect; red arrows).

FIG. 2B Change in cell viability of different types of human renal cellular carcinoma cell (RCC) lines after 5% serum obtained from #301 RCC patient (at day 92 after four cycle JX-594 injection). Asterisk indicate each JX-594 injection.

FIG. 2C Change in cell viability of different types of lung cancer cell lines after 5% serum obtained from #103 lung cancer patient (at day 92 after four cycle JX-594 injection). Asterisk indicate each JX-594 injection.

FIG. 3A. Diagram to show different types of serum from same patient. (a) Base line naïve serum before JX-594 treatment (designated as A serum); (b) Serum obtained at day 92 post JX-594 treatment (designated as B serum); (c) B serum was treated at 56° C. for 30 min for complement heat inactivation (designated as C serum); (d) 50% A serum was added into 50% C serum (designated as D serum). (e) serum was treated by Ig removal resin (ProreoExtract®Albumin/Ig Kit, Calbiochem) column (designated as E serum). FIG. 3B illustrates mean cell viability of human tumor cell lines upon incubation with different preparations of 5% serum, as outlined in FIG. 3A: RCC patient (#301) serum incubated with SNU-349 cells, lung cancer patient (#103) incubated with H460 cells, and melanoma patient (#304) serum incubated with W2664-4 cells.

FIGS. 5A-E. Overall analysis of CDC activity after JX-594 treatment in patients enrolled into Phase 1 (primary and metastatic hepatic mass) and Phase 2 JX-594 clinical trial (Hepatocellular carcinoma). FIG. 5A: Phase 1 patients: Survival vs. reverse of CDC activity in A2780 cells. FIG. 5B: Time dependent CDC change of Phase 2 patients (n=18) in different HCC cell line. FIGS. 5C-5E: CDC profile of serum from CDC responder patients in different human HCC cell lines SUN739 (FIG. 5C), SNU475 (FIG. 5D) or SNU449 (FIG. 5E). Responder was designated <80% cell viability at Day 56 post JX-594 treatment.

DETAILED DESCRIPTION OF THE INVENTION

Figure 1A:
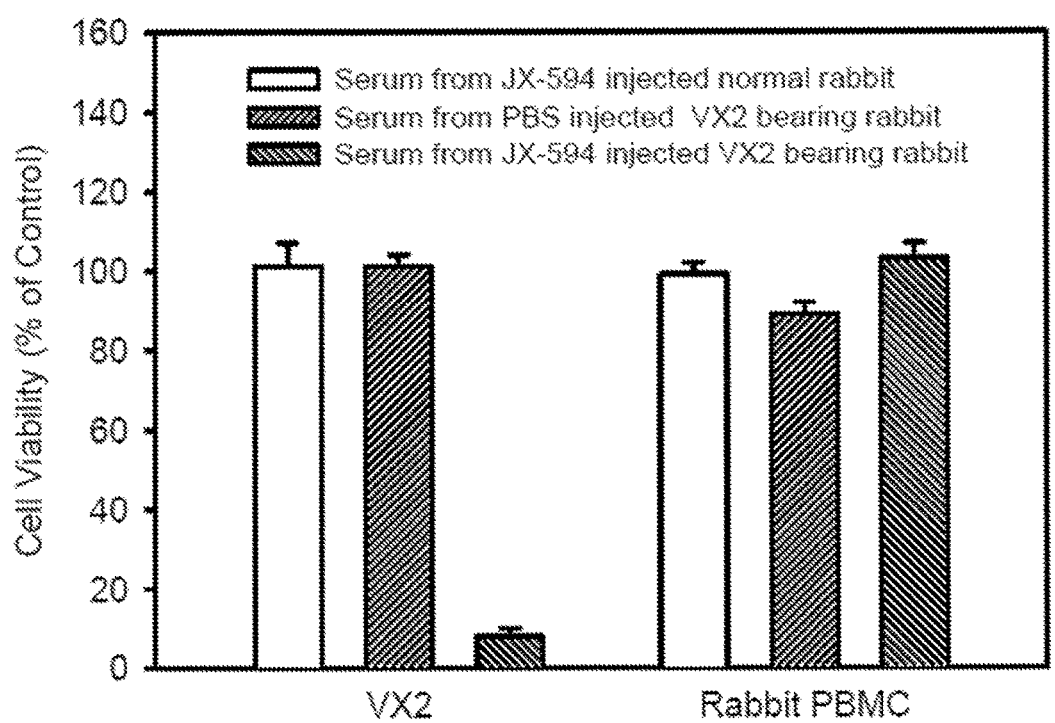

Oncolytic viruses cause virus replication-dependent cancer cytolysis as their primary mechanism of action, yet the induction of cancer-specific immunity can be a major efficacy mediator in preclinical models as well. However, functional anti-cancer immunity induction has not been demonstrated in cancer patients to date. JX-594 is a targeted oncolytic vaccinia virus engineered to express human granulocyte-macrophage colony stimulating factor (GM-CSF) in order to augment the induction of anti-cancer immunity. JX-594 has demonstrated replication and GM-CSF expression, associated with tumor responses in patients on clinical trials.

In the present invention, inventors discovered that JX-594 mediated induction of functional, anti-tumoral immunity induction both in rabbits and subsequently in patients with primary or metastatic liver tumors. Antibody-mediated complement-dependent cancer cell cytotoxicity (CDC) was induced by JX-594 treatment in rabbits and patients with diverse array of tumor types on a Phase 1 trial. CDC induction was subsequently confirmed in patients on a Phase 2 trial in hepatocelluar carcinoma. Significant CDC was still evident even at 1-5% serum in many cases. CDC responses were more common against tumor cell lines of the same histology as that of the patient. Normal cells were resistant to CDC effects. Patients with the longest survival duration had the highest CDC activity. To our knowledge, this is the first proof of 1) the induction of functional anti-cancer immunity by an oncolytic virus in patients, 2) induction of CDC by a therapeutic virus in cancer patients, and 3) the ability of a product to vaccinate patients with a diverse array of tumor types and without reliance on expression of a defined target antigen.

In addition, the inventors performed a SEREX screen was performed to identify target antigens recognized by polyclonal antibodies induced by JX-594 treatment. In addition to direct a cytolytic effect, JX-594 treatment results in the induction of functional systemic cancer-targeting antibodies and CDC in solid tumor patients. Furthermore, treatment with JX-594 can be used as a method to identify relevant tumor antigens in patients with various cancer types.

To briefly further describe the findings upon which the present invention is based, the inventors found that in the Phase 1 clinical trial in patients with treatment-refractory liver tumors, JX-594 demonstrated cancer-specific replication, GM-CSF expression, white blood cell stimulation (neutrophils, eosinophils and monoctyes) and objective cancer responses after intratumoral injections (2-8 total, every three weeks); infection and efficacy against non-injected tumors were also demonstrated[26]. A Phase 2 trial was initiated to evaluate three biweekly intratumoral injections in patients with hepatocellular carcinoma (HCC); preliminary anti-tumoral activity has also been observed on Phase 2 trial. Safety has been acceptable to date, with transient flu-like symptoms being the most common side-effects. An HSV deletion mutant expressing hGM-CSF[27] demonstrated tumor responses to melanoma in a Phase 2 clinical trial.

While virus replication and transgene expression have been reproducibly demonstrated in clinical trials, systemic anti-cancer immunity induction is only beginning to be investigated[28]. However, directly functional immune mechanisms have not been demonstrated. The utility of JX-594 and other immunostimulatory viruses, and the design of future oncolytic products, would be improved dramatically if the anti-cancer immune responses in treated patients could be elucidated. The inventors therefore sought to assess anti-cancer immunity during and after JX-594 therapy.

The inventors additionally evaluated immunity induction in preclinical models and subsequently in patients with liver tumors on both Phase 1 and 2 trials. Archival serum samples obtained at baseline and over time following JX-594 therapy were available for assessment. Antibody-mediated complement-dependent cytotoxicity (CDC) is a potent mechanism of cell killing[30] and CDC activity against tumor cell lines is a direct measure of functional systemic anti-cancer immunity. The inventors also assessed the impact of JX-594 on the induction of antibody-mediated CDC in patients' blood against a panel of tumor cell lines of different histologies over time. The date presented herein provide the first clear demonstration of 1) the induction of functional anti-cancer immunity by an oncolytic virus in patients, 2) induction of CDC by a therapeutic virus in cancer patients, and 3) the ability of a product to vaccinate patients with a diverse array of tumor types and without reliance on expression of a defined target antigen.

This invention is based on the discovery that oncolytic viruses can produce an antibody-mediated tumor specific CDC response. In specific embodiments, it is contemplated that recombinant oncolytic viruses having one or more nucleic acid sequences that encode immunomodulatory polypeptides, such as polypeptides that attenuate the innate immune response or inflammatory response.

In specific studies performed with oncolytic viruses, the inventors demonstrated that virus replication is important in inducing anti-tumor antibodies mediating CDC. Numerous experiments (see FIGS. 9-13 for example) demonstrated lack of CDC induction in serum collected from animals treated with UV inactivated control viruses. Of the various oncolytic viruses used, it was seen that vaccinia virus is best at inducing anti-tumor antibodies mediating CDC, however HSV and VSV also are effective. Specifically, HSV then VSV have an intermediate phenotype but reovirus was not shown to be able to induce CDC in models tested.

Based on virus biology, different levels of CDC response can be observed; and from the data observations, it may be postulated that (enveloped) dsDNA viruses are most potent at inducing anti-tumor antibodies that mediate CDC.

In addition, the studies showed that GM-CSF expression from oncolytic viruses may potentiate ability of virus to induce anti-tumor antibodies mediating CDC. These studies show in principle that immunostimulatory cytokines, of which GM-CSF can be used as an example, expressed in oncolytic oncolytic virus replication may be used to augment the ability of such oncolytic viruses to induce anti-tumor antibodies mediating CDC.

The oncolytic virus may be selected from the group consisting of vesicular stomatitis virus (VSV), Newcastle disease virus (NDV), retrovirus, measles virus, Sinbis virus, influenza virus, herpes simplex virus, vaccinia virus, and adenovirus, or the like, or a recombinant variant thereof. Exemplary oncolytic viruses that may be useful include oncolytic virus selected from the group consisting of JX-594, p53 expressing viruses, reovirus, vesicular stomatitis virus (VSV), ONYX-15, Delta24, adenoviruses mutated in the VA1 region, vaccinia viruses mutated in the K3L or E3L region, Telomelysin, Telomelysin-GFP, parapoxvirus orf viruses mutated in the OV20.0L gene, and herpes viruses mutated in the ☐134.5 gene. In specific exemplary embodiments the oncolytic virus is JX-594.

The heterologous nucleic acid sequence may be any therapeutic protein that is to be delivered by the oncolytic virus.

In still another embodiment, the recombinant oncolytic virus further comprises one or more heterologous viral internal ribosome entry site (IRES) that is neuronally-silent and operably linked to at least one nucleic acid sequence that encodes an oncolytic virus polypeptide needed for virus gene expression, replication or propagation, such as a polymerase (e.g., viral RNA-dependent RNA polymerase or DNA polymerase); a structural protein (e.g., nucleocapsid protein, phosphoprotein, or matrix protein); or a glycoprotein (e.g., envelope protein). In a further embodiment, the recombinant oncolytic virus has two or three IRESs and each is operably linked to a different nucleic acid sequence that encodes an oncolytic virus polypeptide. For example, one IRES may be linked to an oncolytic virus polymerase and a second IRES may be linked to a structural protein or a glycoprotein. In yet a further embodiment, the recombinant oncolytic virus has a first IRES operably linked to a nucleic acid sequence that encodes an oncolytic virus polymerase; a second IRES operably linked to a nucleic acid sequence that encodes an oncolytic virus glycoprotein; and a third IRES operably linked to a nucleic acid sequence that encodes an oncolytic virus structural protein. In another embodiment, the IRES is a picornavirus IRES, such as a type I IRES from a Rhinovirus, such as a human Rhinovirus 2, or a Foot and Mouth Disease virus or any combination thereof.

In specific aspects of the present invention, the oncolytic virus is used to induce a tumor-specific antibody mediated complement-dependent cytotoxic response in an animal having a tumor comprising administering to said animal a composition comprising a replication competent oncolytic virus wherein administration of said composition produces antibodies that mediate a CDC response specific to said tumor. In doing so the oncolytic virus may be used in order to inhibit the growth or promote the killing of a tumor cell.

The methods generally will comprise administering the recombinant oncolytic virus at a multiplicity of infection sufficient to induce a tumor-specific antibody mediated CDC response in the animal to which it is administered. The tumor cell may be any tumor cell against which an anti-tumor response is desired. The cell may be contacted with the oncolytic virus in vivo, ex vivo, or in vitro.

In some embodiments, the oncolytic virus is administered to an animal in vivo. The administration may be intravascularly into a vein or an artery. For example, in the case of a hepatic tumor, the oncolytic virus may be administered to a hepatic artery via an in-dwelling medical device such as a catheter. In other embodiments, the recombinant oncolytic virus may be administered intravascularly, intratumorally, or intraperitoneally.

In specific embodiments, the methods of the invention relate to treatment of a cancer in a human patient by generating in said human a tumor-specific antibody mediated CDC response against the specific tumor experienced by said human. For example, such methods comprise the step of administering one or more oncolytic virus as described herein at an MOI that is sufficient to produce a tumor-specific antibody mediated CDC response. It is contemplated that this response will be sufficient to retard the growth of and/or kill a tumor cell in the human patient. In some embodiments, the response will be useful in treating a tumor in situ by directly administering to the patient the oncolytic virus. In other embodiments, it is contemplated that the tumor cells of the subject are removed and a tumor-specific antibody mediated CDC response is generated against said tumor cells ex vivo. The antibodies produced in this ex vivo response are then administered to the tumor patient in an autologous therapy for the cancer in the subject. Alternatively, the antibodies produced may be administered to a different subject than the individual from whom the tumor cells are initially obtained.

It should be understood that the use of oncolytic viruses described herein for generating a tumor-specific antibody mediated CDC response will find utility in the treatment of a wide range of tumor cells or cancers including, for example, breast cancer (e.g., breast cell carcinoma), ovarian cancer (e.g., ovarian cell carcinoma), renal cell carcinoma (RCC), melanoma (e.g., metastatic malignant melanoma), prostate cancer, colon cancer, lung cancer (including small cell lung cancer and non-small cell lung cancer), bone cancer, osteosarcoma, rhabdomyosarcoma, leiomyosarcoma, chondrosarcoma, pancreatic cancer, skin cancer, fibrosarcoma, chronic or acute leukemias including acute lymphocytic leukemia (ALL), adult T-cell leukemia (T-ALL), acute myeloid leukemia, chronic myeloid leukemia, acute lymphoblastic leukemia, chronic lymphocytic leukemia, lymphangiosarcoma, lymphomas (e.g., Hodgkin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), Castleman's disease, Kaposi's Sarcoma, hemangiosarcoma, multiple myeloma, Waldenstrom's macroglobulinemia and other B-cell lymphomas, nasopharangeal carcinomas, head or neck cancer, myxosarcoma, liposarcoma, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, cervical carcinoma, vaginal carcinoma, vulvar carcinoma, transitional cell carcinoma, esophageal cancer, malignant gastrinoma, small intestine cancer, cholangiocellular carcinoma, adenocarcinoma, endocrine system cancer, thyroid gland cancer, parathyroid gland cancer, adrenal gland cancer, sarcoma of soft tissue, urethral, penile cancer, testicular cancer, malignant teratoma, solid tumors of childhood, bladder cancer, kidney or ureter cancer, carcinoma of the renal pelvis, malignant meningioma, neoplasm of the central nervous system (CNS), tumor angiogenesis, spinal axis tumor, pituitary adenoma, epidermoid cancer, squamous cell cancer, environmentally induced cancers including those induced by asbestos, e.g., mesothelioma, and combinations of these cancers.

It should further be understood that the oncolytic virus may comprise any heterologous nucleic acid that may need to be delivered to the subject.

The term "therapeutically effective amount" or "effective amount" refers to an amount of a recombinant oncolytic virus composition sufficient to reduce, inhibit, or abrogate tumor cell growth, either in vitro or in a subject (e.g., a human, primate, dog, pig or cow). As noted herein, the reduction, inhibition, or abrogation of tumor cell growth may be the result of necrosis, apoptosis, or an immune response. The amount of a recombinant oncolytic virus composition that is therapeutically effective may vary depending on the particular oncolytic virus used in the composition, the age and condition of the subject being treated, or the extent of tumor formation, and the like.

The recombinant oncolytic virus to be used in the methods of the invention may be administered in a convenient manner such as by the oral, intravenous, intra-arterial, intra-tumoral, intramuscular, subcutaneous, intranasal, intradermal, or suppository routes or by implantation (e.g., using slow release molecules). Depending on the route of administration of an adjunctive therapy, like an immunotherapeutic agent, the agents contained therein may be required to be coated in a material to protect them from the action of enzymes, acids and other natural conditions which otherwise might inactivate the agents. In order to administer the composition by other than parenteral administration, the agents will be coated by, or administered with, a material to prevent inactivation.

The recombinant oncolytic virus of the present invention may also be administered parenterally or intraperitoneally. Dispersions of the recombinant oncolytic virus component may also be prepared in, including but not limited to, glycerol, liquid polyethylene glycols, and mixtures thereof and in oils. Under ordinary conditions of storage and use, these preparations may contain a preservative to prevent the growth of microorganisms, such as an antibiotic like gentamycin.

As used herein "pharmaceutically acceptable carrier and/or diluent" includes any and all solvents, dispersion media, coatings, antibacterial and antifungal agents, isotonic and absorption delaying agents and the like. The use of such media and agents for biologically active substances is well known in the art. Supplementary active ingredients, such as antimicrobials, can also be incorporated into the Compositions.

The carrier can be a solvent or dispersion medium containing, for example, water, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be effected by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the recombinant oncolytic viruses of the present disclosure in the required amount of the appropriate solvent with various other ingredients enumerated herein, as required, followed by suitable sterilization means. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum drying and freeze-drying techniques, which yield a powder of the recombinant oncolytic virus plus any additional desired ingredient from a previously sterile-filtered solution thereof.

It may be advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically or veterinary acceptable carrier.

Pharmaceutical compositions comprising the recombinant oncolytic virus of this disclosure may be manufactured by means of conventional mixing, dissolving, granulating, dragee-making, levigating, emulsifying, encapsulating, entrapping or lyophilizing processes. Pharmaceutical viral compositions may be formulated in conventional manner using one or more physiologically acceptable carriers, diluents, excipients or auxiliaries that facilitate formulating active recombinant oncolytic virus into preparations that can be used biologically or pharmaceutically. The recombinant oncolytic virus compositions can be combined with one or more biologically active agents and may be formulated with a pharmaceutically acceptable carrier, diluent or excipient to generate pharmaceutical or veterinary compositions of the instant disclosure.

Pharmaceutically acceptable carriers, diluents or excipients for therapeutic use are well known in the pharmaceutical art, and are described herein and, for example, in Remington's Pharmaceutical Sciences, Mack Publishing Co. (A. R. Gennaro, ed., 18.sup.th Edition (1990)) and in CRC Handbook of Food, Drug, and Cosmetic Excipients, CRC Press LLC (S. C. Smolinski, ed. (1992)). In certain embodiments, recombinant oncolytic virus compositions may be formulated with a pharmaceutically or veterinary-acceptable carrier, diluent or excipient is aqueous, such as water or a mannitol solution (e.g., about 1% to about 20%), hydrophobic solution (e.g., oil or lipid), or a combination thereof (e.g., oil and water emulsions). In certain embodiments, any of the biological or pharmaceutical compositions described herein have a preservative or stabilizer (e.g., an antibiotic) or are sterile.

The biologic or pharmaceutical compositions of the present disclosure can be formulated to allow the recombinant oncolytic virus contained therein to be bioavailable upon administration of the composition to a subject. The level of recombinant oncolytic virus in serum, tumors, and other tissues after administration can be monitored by various well-established techniques, such as antibody-based assays (e.g., ELISA). In certain embodiments, recombinant oncolytic virus compositions are formulated for parenteral administration to a subject in need thereof (e.g., a subject having a tumor), such as a non-human animal or a human. Preferred routes of administration include intravenous, intra-arterial, subcutaneous, intratumoral, or intramuscular.

Proper formulation is dependent upon the route of administration chosen, as is known in the art. For example, systemic formulations are an embodiment that includes those designed for administration by injection, e.g. subcutaneous, intra-arterial, intravenous, intramuscular, intrathecal or intraperitoneal injection, as well as those designed for intratumoral, transdermal, transmucosal, oral, intranasal, or pulmonary administration. In one embodiment, the systemic or intratumoral formulation is sterile. In embodiments for injection, the recombinant oncolytic virus compositions of the instant disclosure may be formulated in aqueous solutions, or in physiologically compatible solutions or buffers such as Hanks's solution, Ringer's solution, mannitol solutions or physiological saline buffer. In certain embodiments, any of the recombinant oncolytic virus compositions described herein may contain formulator agents, such as suspending, stabilizing or dispersing agents. In embodiments for transmucosal administration, penetrants, solubilizers or emollients appropriate to the harrier to be permeated may be used in the formulation. For example, 1-dodecylhexahydro-2H-azepin-2-one (Azon®), oleic acid, propylene glycol, menthol, diethyleneglycol ethoxyglycol monoethyl ether (Transcutol®), polysorbate polyethylenesorbitan monolaurate (Tween®-20), and the drug 7-chloro-1-methyl-5-phenyl-3H-1,4-benzodiazepin-2-one (Diazepam), isopropyl myristate, and other such penetrants, solubilizers or emollients generally known in the art may be used in any of the compositions of the instant disclosure.

Administration can be achieved using a combination of routes, e.g., first administration using an intra-arterial route and subsequent administration via an intravenous or intratumoral route, or any combination thereof.

In specific embodiments, the present disclosure provides methods of generating in vivo antibodies that mediate an anti-tumor CDC response comprising administering to a subject a composition comprising a replication competent oncolytic virus wherein administration of said composition produces antibodies that mediate a CDC response specific to the tumor. It has been shown by the inventors that the tumor-specific antibody mediated anti-tumor CDC response generated by administration of replication competent oncolytic virus may be used to inhibit the growth or even kill cancer cells. Thus, by administering a recombinant oncolytic virus according to the instant disclosure at a multiplicity of infection sufficient to generate a tumor-specific CDC response in the animal will inhibit the growth of a tumor cell or to kill a tumor cell. In certain embodiments, the recombinant oncolytic virus is administered more than once, preferably twice, three times, or up to 10 times. In certain other embodiments, the tumor cell is treated in vivo, ex vivo, or in vitro.

Examples of tumor cells or cancers that may be treated using the methods of this disclosure include hepatic cell carcinoma, breast cancer (e.g., breast cell carcinoma), ovarian cancer (e.g., ovarian cell carcinoma), renal cell carcinoma (RCC), melanoma (e.g., metastatic malignant melanoma), prostate cancer, colon cancer, lung cancer (including small cell lung cancer and non-small cell lung cancer), bone cancer, osteosarcoma, rhabdomyosarcoma, leiomyosarcoma, chondrosarcoma, pancreatic cancer, skin cancer, fibrosarcoma, chronic or acute leukemias including acute lymphocytic leukemia (ALL), adult T-cell leukemia (T-ALL), acute myeloid leukemia, chronic myeloid leukemia, acute lymphoblastic leukemia, chronic lymphocytic leukemia, lymphangiosarcoma, lymphomas (e.g., Hodgkin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), Castleman's disease, Kaposi's Sarcoma, hemangiosarcoma, multiple myeloma, Waldenstrom's macroglobulinemia and other B-cell lymphomas, nasopharangeal carcinomas, head or neck cancer, myxosarcoma, liposarcoma, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, cervical carcinoma, vaginal carcinoma, vulvar carcinoma, transitional cell carcinoma, esophageal cancer, malignant gastrinoma, small intestine cancer, cholangiocellular carcinoma, adenocarcinoma, endocrine system cancer, thyroid gland cancer, parathyroid gland cancer, adrenal gland cancer, sarcoma of soft tissue, urethral, penile cancer, testicular cancer, malignant teratoma, solid tumors of childhood, bladder cancer, kidney or ureter cancer, carcinoma of the renal pelvis, malignant meningioma, neoplasm of the central nervous system (CNS), tumor angiogenesis, spinal axis tumor, pituitary adenoma, epidermoid cancer, squamous cell cancer, environmentally induced cancers including those induced by asbestos, e.g., mesothelioma, and combinations of these cancers.

Given that the invention shows it is possible to raise an antibody mediated tumor-specific CDC response in cancer patients by treating the patient with a replication competent oncolytic virus, the inventors have discovered that it will be possible to specifically tailor a cancer therapy for a subject having cancer comprising by administering to the subject a composition that comprises the replication competent oncolytic virus to produce antibodies that mediate a CDC response specific to said cancer in said subject. Once this response is generated the serum containing the tumor specific antibodies and B cells against the cancer are harvested from the subject and expanded ex vivo. This expanded population of antibodies and/or harvested B cells producing those antibodies are uses as an immunotherapy composition that is specific for the cancer patient. As such, this immunotherapy can be administered to the subject to produce an anti-cancer effect. The immunotherapy composition can be prepared and administered to the subject immediately upon isolation of the antibodies or it can be stored for further treatment at a later stage in the therapy of the subject.

Methods of ex vivo expansion of B cells and antibodies are well known to those of skill in the art and simply involve growth of the antibody producing cells in culture and harvesting of the antibodies using standard protein purification techniques.

In still another embodiment, the methods involve parenteral administration of a recombinant oncolytic virus, preferably via an artery or via an in-dwelling medical device. As noted above, the recombinant oncolytic virus can be administered with an immunotherapeutic agent or immunomodulator, such as an antibody that binds to a tumor-specific antigen (e.g., chimeric, humanized or human monoclonal antibodies). In another embodiment, the recombinant oncolytic virus treatment may be combined with surgery (e.g., tumor excision/resection), radiation therapy, chemotherapy, or immunotherapy, and can be administered before, during or after a complementary treatment.

For example, it is contemplated that the methods of the invention comprise generating an antibody mediated tumor-specific CDC response by administering an oncolytic virus to the subject wherein in combination with administration of the oncolytic virus the subject is treated with an additional cancer therapy to the human. In a specific embodiment, the additional cancer therapy is chemotherapy, radiation, surgery, immunotherapy, gene therapy, or a combination thereof. In specific embodiments, the cancer cell is in a human and/or the introduction step is further defined as administering at least about $1 \times 10^9$ plaque forming units (pfu) of the oncolytic virus to the human.

It has been estimated that approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy such as administration of the oncolytic viruses described herein. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages.

In the therapeutic methods of the invention the oncolytic virus is used to produce an antibody-mediated response to a tumor or cancer in a subject. The response is sufficient to produce the treatment of the cancer or tumor, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, the antibodies or B cells producing the antibodies may be used in combination with conventional anticancer therapies to provide a combined effect to kill or inhibit proliferation of the cell.

The following non-limiting examples are provided to illustrate various aspects of the present disclosure. All references, patents, patent applications, published patent applications, and the like are incorporated by reference in their entireties herein.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Methods

Viruses and Cell Lines:

JX-594, Wyeth strain vaccinia virus (Thymidine Kinase [TK]-inactivated, expressing hGM-CSF) was used throughout this study and was prepared as published previously[24]. SNU349, SUN482 and SNU267 (human renal cell carcinoma; obtained from Korean Cell Line Bank [KCLB]) and SNU475 & SNU398 (human hepatocelluar carcinoma; obtained from KCLB), were cultured in RPMI 1640 (Gibco) supplemented with 10% FBS (Hyclone) with penicillin and streptomycin. HOP62, H157, H460 and PC10 (human lung carcinoma; obtained from American Type Culture Collection [ATCC]), HepG2 (human hepatocelluar carcinoma; obtained from ATCC), SF-295 (human gall bladder cancer; obtained from ATCC), PC-3 (human prostate cancer; obtained from ATCC), PANC-1 (human pancreatic cancer; ATCC), MCF-7 (human breast cancer; ATCC) were cultured in DMEM medium containing 10% FBS with penicillin and streptomycin. MRC-5 nontransformed cells (lung fibroblast; ATCC) and HUVEC (endothelial cells; ATCC) MRC-5 were cultured in endothelial cell medium EBM-2 (Lonza, Md., USA) supplemented with 2% fetal bovine serum (FBS) with penicillin and streptomycin.

Rabbit VX2 Tumor Model and Isolation of VX2 Cells:

VX2 tumors were grown and maintained in the muscle of inbred New Zealand white rabbit (Samtako, Oh-San, Korea). JX-594 ($1 \times 10^9$ pfu) or Phosphate-buffered saline (PBS) was injected at 3 weeks and 4 weeks post VX2 fragment implantation into skeletal muscle. Serum was collected at baseline, 3 weeks and 6 weeks post JX-594 or PBS treatment. VX2 was isolated as described previously[31]. In brief, VX2 cells were isolated from VX2 tissues enzymatically (collagenase 0.01% protease 0.1% overnight at 4° C.), and maintained in vitro with Dulbecco's modified Eagle's medium (DMEM) with 10% fetal bovine serum (FBS) for 8 passages. Fresh VX2 cells were used for each cell viability test. In a parallel study, JX-594 was injected into a normal, non-tumor-bearing rabbit, and serum was obtained.

Cell Viability & CDC Assay:

Cell viability was decreased when serum was added into (not heat treatment). CDC activity was assessed by measuring cell viability upon incubation with 5% serum in 96 well plates. Cell viability in serum post JX-594 administration was normalized to the cell viability of rabbit or patient serum at baseline (prior to JX-594 treatment). Each cell line was seeded onto 96-well plates and incubated overnight. Cells were subsequently incubated with DMEM (no FBS) and the serum sample at 37° C. for 4 hours. Cells were subsequently exposed to PBS and 10 μl Cell counting kit-8 (CCK-8) solution (CCK-8 kit, Dojindo, Inc., Kumamoto, Japan) and incubated at 37° C. for 2 hours. Cell viability was measured by optical density at 450 nm.

Western Blotting:

VX2 cells, rabbit peripheral blood mononuclear cells, SNU349 or SNU739 cells were lysed at $1 \times 10^6$ cells/mL in PRO-PREP™ protein extraction solution (iNtRON Biotechology, Korea) on ice for 30 min. After centrifugation, 50 μg of protein were separated using SDS-PAGE gels and transferred to PVDF membrane (Immunobilon-P; Millipore, Billerica, Mass.). Sera were diluted 1/100 in 0.1% TBST (5% skim milk powder; 0.1% Tween 20; 50 mmol/L Tris; 150 mmol/L NaCl) and incubated on PVDF membranes for 90 minutes at room temperature. The membrane was then incubated for 1 h at room temperature with horseradish peroxidase-conjugated goat anti-rabbit IgG (Stanta Cruz) diluted 1/10,00 in 0.1% TBST (rabbit serum primary) or anti-human IgG (Sigma #A1543, 1:5,000) (human serum primary) and visualized by enhanced chemiluminescence (ECL kit; Pierce, Rockford, Ill.).

Fluorescence & Confocal Microscopy:

Each cell line was plated into 6-well plates and cells were incubated for 24 h to reach 100% cell density. For fluorescence staining, SNU349 cells were seeded into coverglass-bottom dish at $3 \times 10^5$ cells and left overnight. Carboxyfluorescein succinimidyl ester (CSFE) and 7-amino-actinomycin D (7-AAD) (ACT 1™ Assay for CytoToxicity, Cell Technology) were added to stain viable and dying cells, respectively. In live cells, CSFE (green fluorescence in whole cells) can be detected while red fluorescence can be detected in nucleus of dead cells.

SEREX Study:

A cDNA library was constructed from mRNA extracted from SNU449, a human hepatocellular carcinoma (HCC) cell line. The cDNA library was cloned into a λ ZAP expression vector (ZAP-cDNA Synthesis Kit, [Stratagene CA]). The titer of amplified library was $1 \times 10^9$ pfu/ml, and $5 \times 10^5$ pfu was used for primary immunoscreening against human serum. Phage plaques appeared after 6-8 h incubation at 42° C. and then transferred into 132 mm nitrocellulose membranes (Millipore, Bedford) which were soaked in 10 mM IPTG (Sigma-Aldrich, USA) for 30 min previously. The nitrocellulose membranes were blocked with 5% BSA (Santa Cruz, USA). Pooled serum from JX-594 treated HCC patients (D57 post JX-594 injection) was used for primary and secondary screening. The serum from patients with the highest CDC activity was pooled for this study (patients #1702, #1703, #1704, #1705, #1712, #1713 and #1715). Pooled serum was added (6 ml of 1:100 diluted serum) for primary antibody screening, bound antibody detected with 1:5000 diluted alkaline phosphatase labeled goat anti-human IgG (Sigma-Aldrich, USA) and then the membrane was developed with BCIP/NBT solution, premixed (Sigma-Aldrich, USA). Blue plaques were cored from the agar plate corresponding to the membranes and put into SM buffer 100 mM NaCl, 50 mM Tris-HCl (pH7.5), 10 mM MgSO$_4$) containing 20 μl chloroform. After 70 plates were screened (5 plates for 1 round), we isolated 70 positive plaques. After a second round of screening (82 mm plate), 11 plaques were purified to monoclonality (>90% positive phages with high density). After DNA extraction from each clone, DNA was sequenced.

Dot Blotting:

E. coli phage lysates for each positive clone was diluted 5 fold in SM buffer and 1 μL of diluted lysates were spotted on test strip of Whartman membrane (Whartman, Germany). After air dry for 5 min, all test strips were immersed in blocking solution for 1 h. Membranes were incubated in 1:50 JX-594 preinjected (0 week, 2 week, 4 week) or postinjected (D57) human serum for 1 h. Bound antibody was detected with 1:2500 diluted alkaline phosphatase labeled goat anti-human IgG (Sigma-Aldrich, USA) and developed with BCIP/NBT solution.

Example 2: CDC is Induced in Both Animal Models and in Human Patients

Decreased Cell Viability Observed Upon Incubation of Tumor Cells with Serum from Tumor-Bearing, JX-594-Treated Rabbits.

Figure 1D:
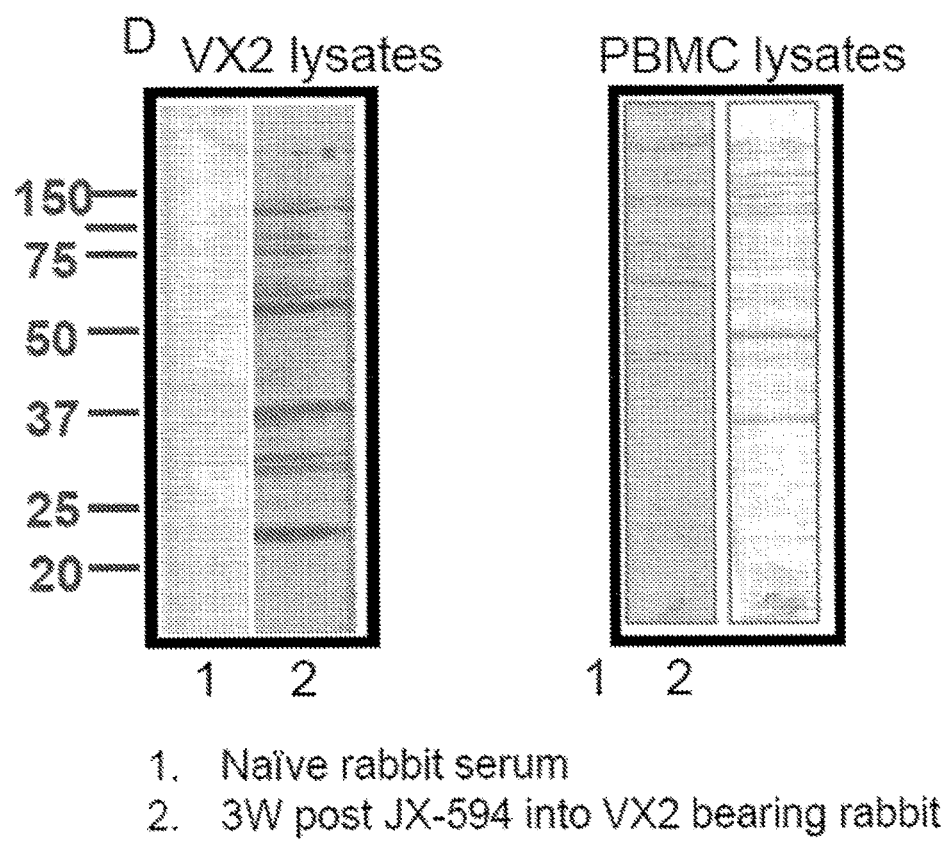

To investigate induction of CDC in a rabbit model, serum was collected from rabbits bearing the VX2 adenocarcinoma implanted into muscle treated with JX-594 or PBS control. Serum collected at day 28 post injection was added to VX2 cells or rabbit peripheral blood mononuclear cells (PBMCs) in vitro at a concentration of 3%. A significant decrease (approximately 90%) in cell viability was only observed in cells incubated with serum from JX-594-treated, VX2 tumor-bearing rabbits (FIG. 1a). Incubation of VX2 cells with serum from VX2 tumor-bearing rabbits treated with PBS or non-tumor-bearing rabbits treated with JX-594 did not exhibit decreased cell viability. Furthermore, PBMC viability did not decrease significantly upon incubation with serum from any treatment group. VX2 cell viability was subsequently assessed upon incubation with serum collected at various timepoints post JX-594 (or PBS) injection. Decreased VX2 cell viability upon incubation with serum collected from Day 18 onward in VX2 tumor-bearing, JX-594-treated rabbits (FIG. 1b). Increased concentration of serum (up until 2%) resulted in dose-dependent decreases in VX2 cell viability (FIG. 1c). Incubation of cells with 2% serum resulted in approximately 20% VX2 cell viability when compared to treatment with normal rabbit serum control. In order to assess whether serum from VX2-bearing, JX-594-treated rabbits binds novel antigens, a Western blot was carried out on VX2 and PBMC cell lysates with serum from naïve rabbits and JX-594-treated tumor-bearing rabbits. Strong reactivity to new antigens was only observed in the VX2 cell line lysate and multiple new bands were recognized upon JX-594 treatment of VX2 tumor-bearing rabbits, indicating an induction of polyclonal antibodies to VX2 tumor antigens (FIG. 1d).

Evidence of Decreased Cell Viability Upon Incubation of Human Cancer Cell Lines with Serum from JX-594-Treated Patients Upon detection of significant decreases in cell viability triggered by incubation with rabbit serum from JX-594-treated, tumor-bearing rabbits, we sought to identify whether a similar activity could be observed in serum collected from JX-594-treated patients. The inventors began by testing serum from two patients treated on the Phase 1 liver tumor trial who had significant responses and long-term survival after JX-594 therapy (patient 103: lung cancer, 24.5 months survival; patient 301: renal cell cancer, 44.1+months survival)[26]. Indeed, similar to observation in the preclinical model, incubation of cancer cell lines with JX-594-treated patient serum (5%) resulted in significant decreases in cell viability (FIG. 2a). Cancer cell lines of the same origin as the patients' cancer were tested and a time-dependent decrease in cell viability was observed in most cell lines. Visualization of cells under bright field microscopy revealed formation of membrane attack complexes (MAC), which indicated the decrease cell viability is triggered by CDC (FIG. 2b). CSFE and 7-AAD dyes were used to stain live and dead cells, respectively. 7-AAD staining demonstrates cells treated with serum from JX-594 immune patients are undergoing cell death.

Figure 3A:
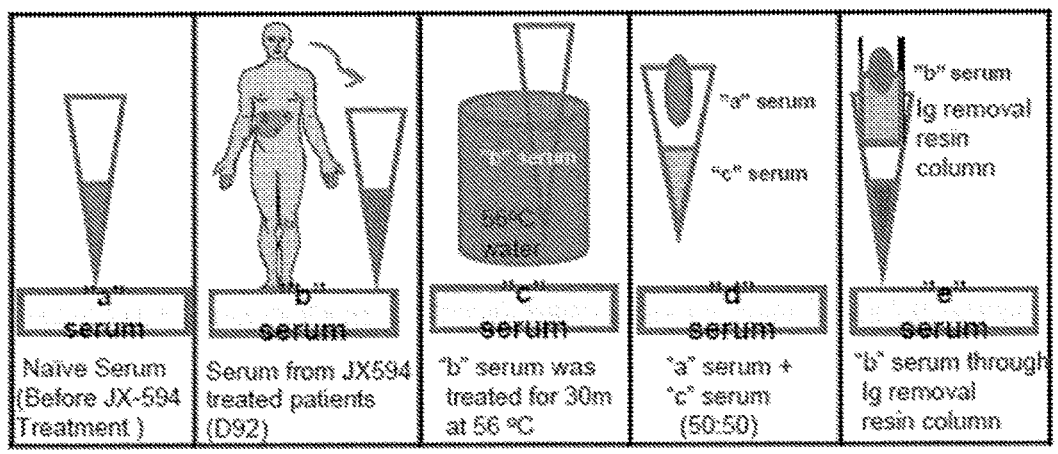
FIGS. 3A-B. Evidence for generation of antibody-mediated complement-dependent cancer cell cytolysis after JX-594 multiple treatment in treatment-refractory solid tumor patients.
Figure 3B:
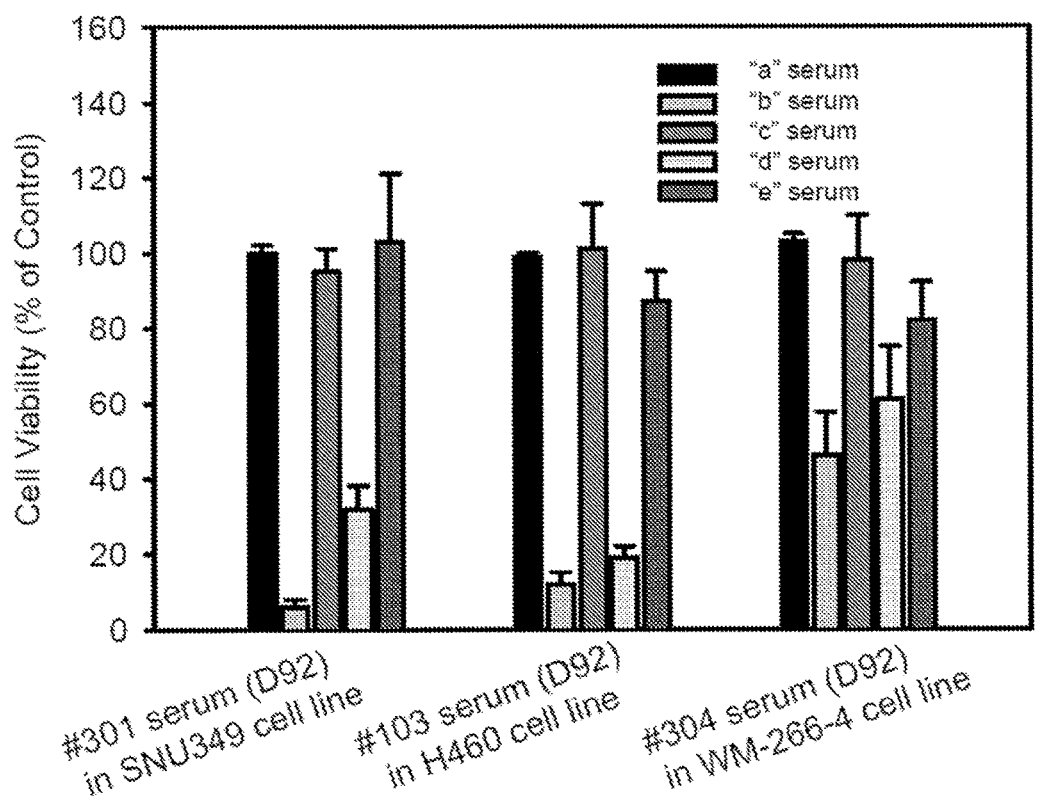
Figure 3C:
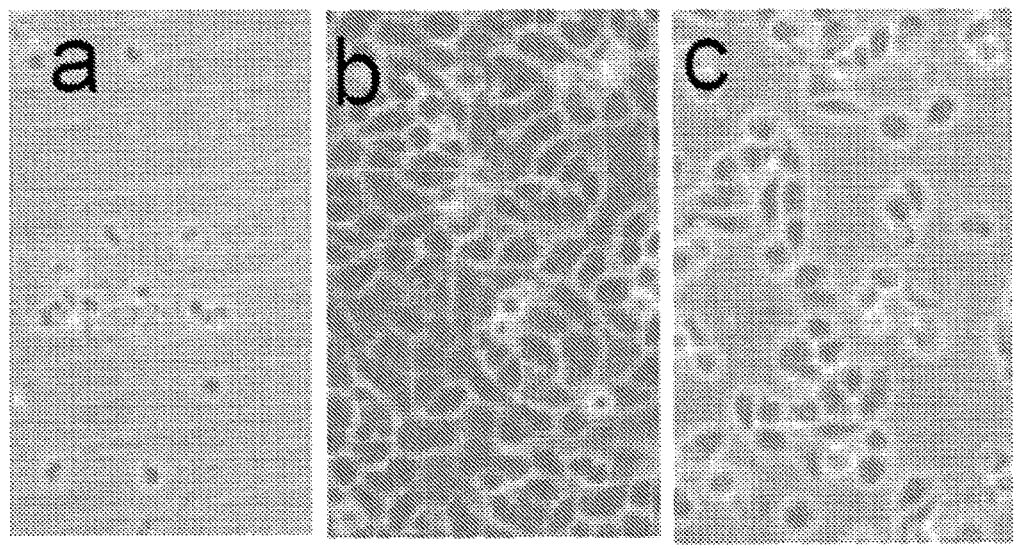
FIG. 3C. Representative light microscopy of human cancer cell line after treatment of B, C or D serum (5% for each). Photomicroscopy was taken at 4 hour post treatment of B, C or D serum obtained from #301 RCC patient in SNU349 RCC cell line.
Figure 3D:
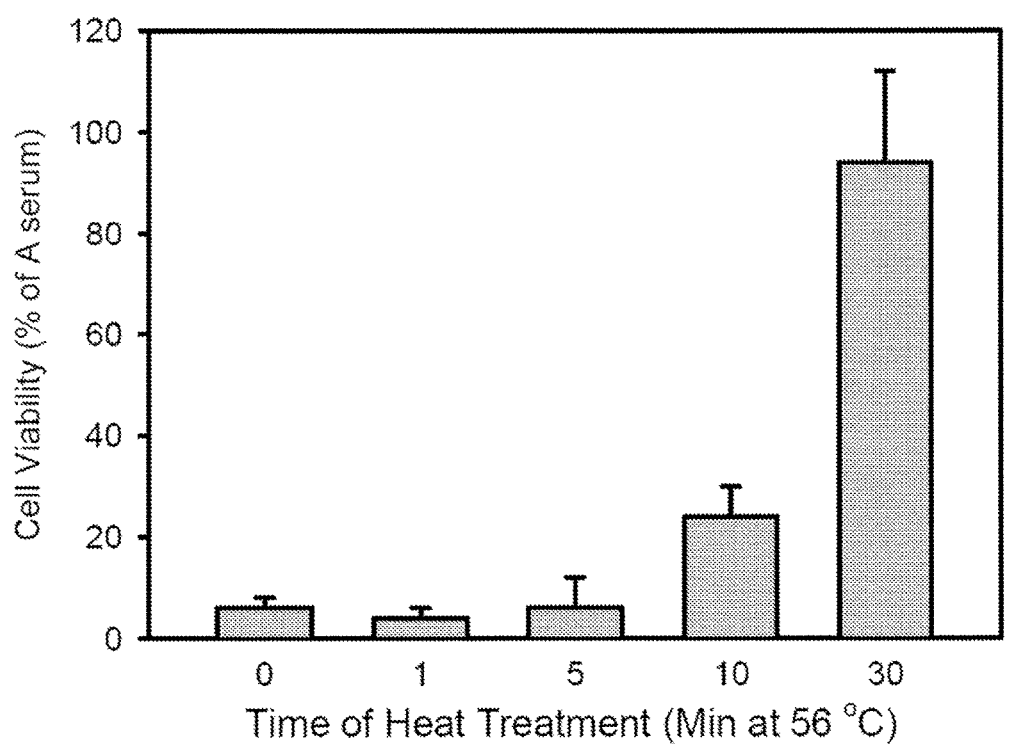
FIG. 3D Effect of duration of heat treatment in loss of cancer cell killing ability. (a) After addition of same volume of Naïve serum (A serum) into heat inactivated C serum, this mixture serum was added into cultured A2790 or SNU349 cells. The killing effect of serum was significantly recovered suggesting complement addition into cancer specific antibody containing B serum. In CDC, antigen-antibody complex is major activator of complement. Antibody determines target specificity while complement activation induce cell lysis via formation of membrane attack complex (MAC). (b) Finally B serum was eluted by IgG removal column (ProreoExtract®Albumin/Ig Kit, Calbiochem) which caused loss of killing activity suggesting IgG may be critical for CDC.
Figure 4A:
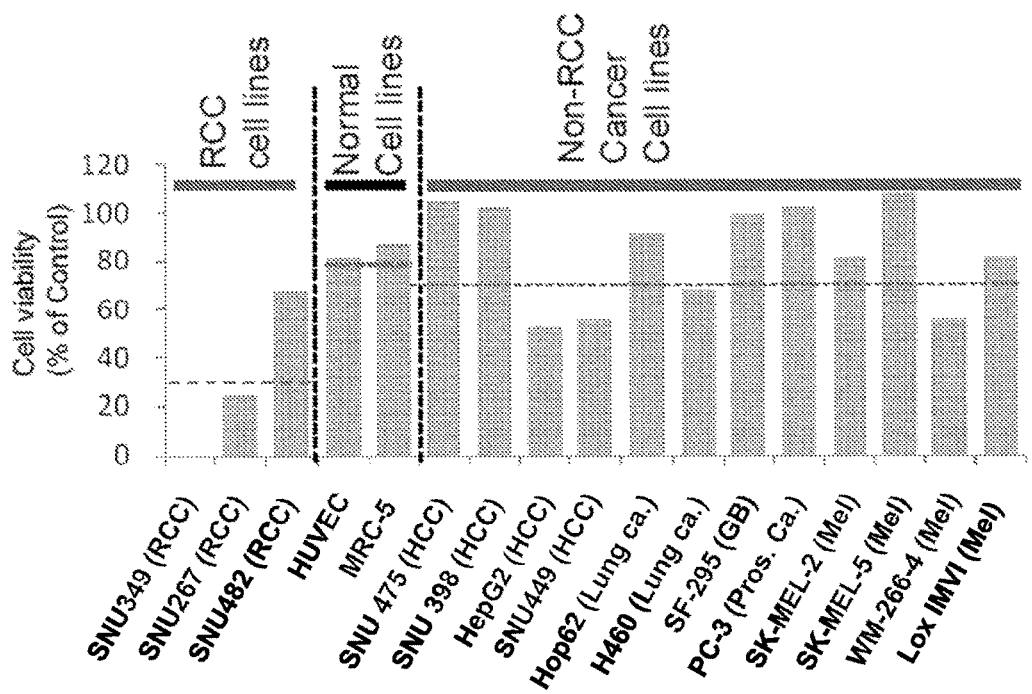
FIGS. 4A-D Profile of complement dependent cytotoxicity (CDC) for selected JX-594 treated patients in different types of human cancer cell lines. CDC activity was displayed as reverse ratio of cell viability by 5% serum (archival samples of day 42-92 and day 56 post JX-594 treatment for phase 1 patients and for phase 2 patients were used) to by baseline naïve 5% serum from each patient. Profile of CDC activity in different human cancer cell lines and normal cell lines by serum from JX-594 treated #301 RCC (FIG. 4A), #304 melanoma (FIG. 4B), #1702 HCC (FIG. 4C), and #1705 HCC (FIG. 4D) patients.
Figure 4B:
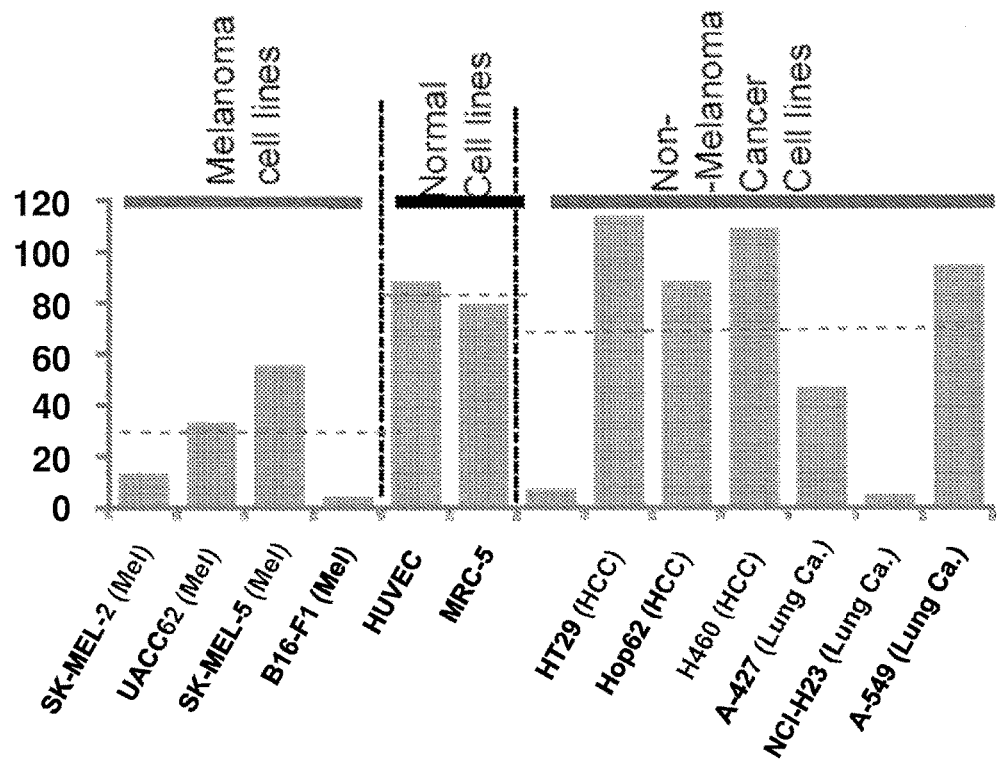
Figure 4C:
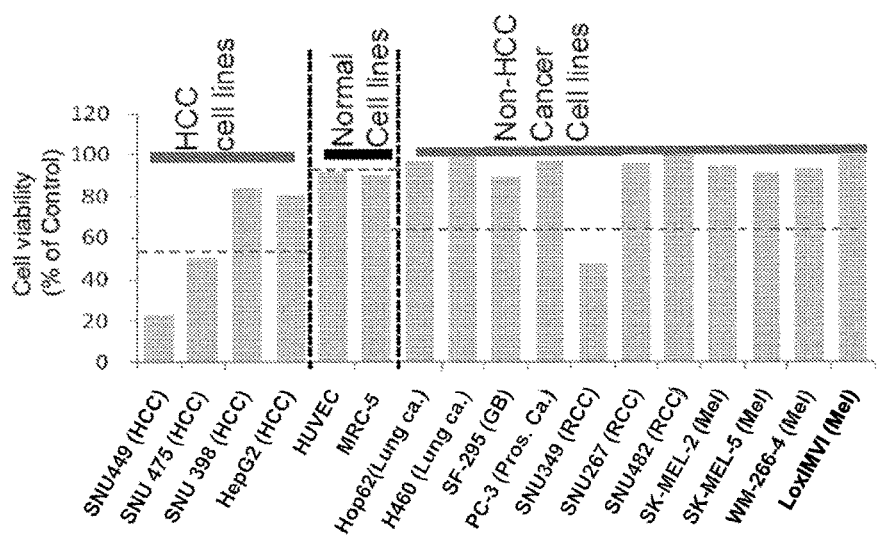
Figure 4D:
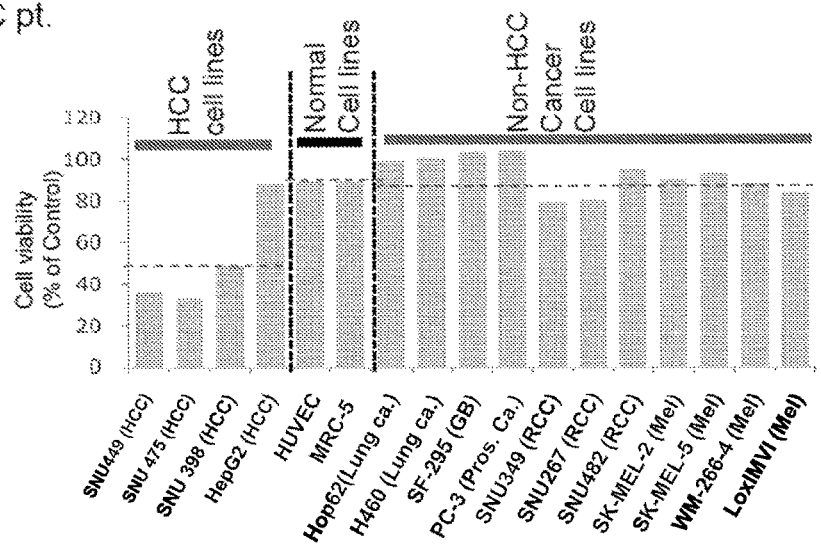
Figure 4D:
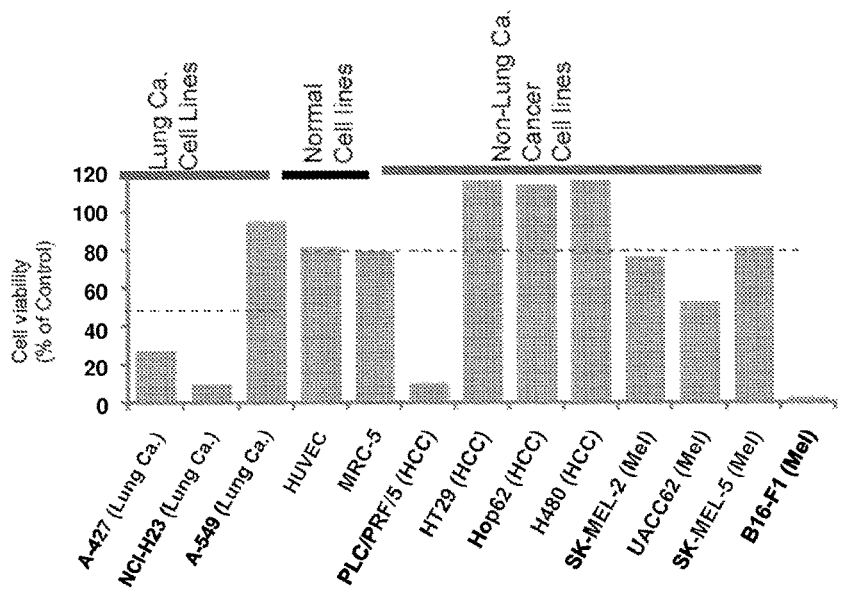
Figure 5B:
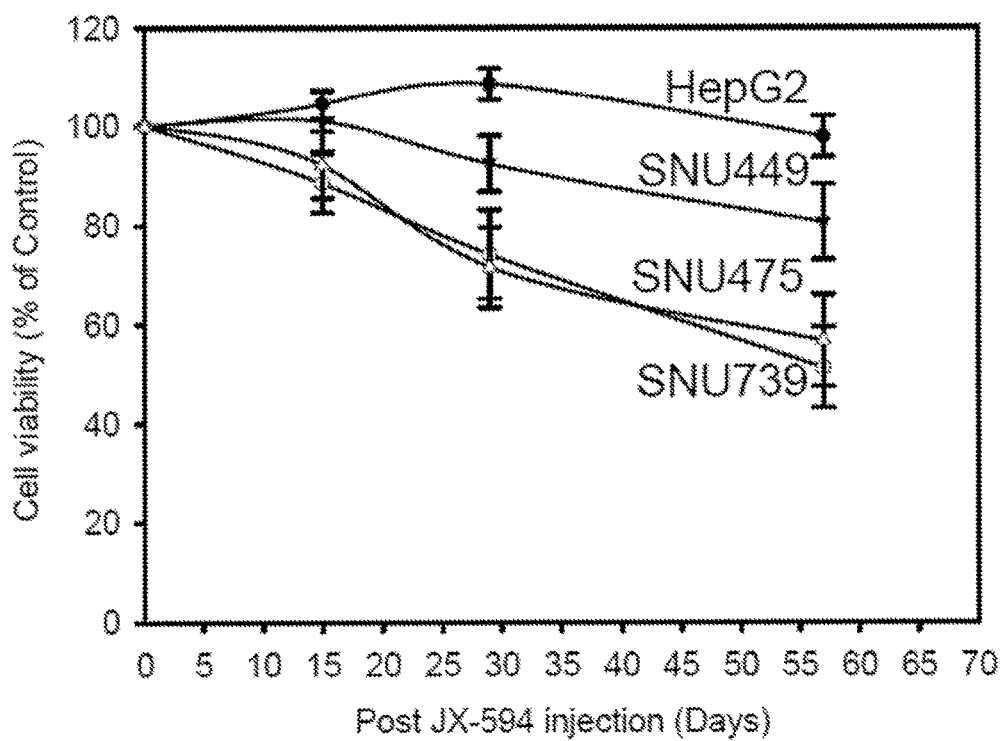
Figure 5C:
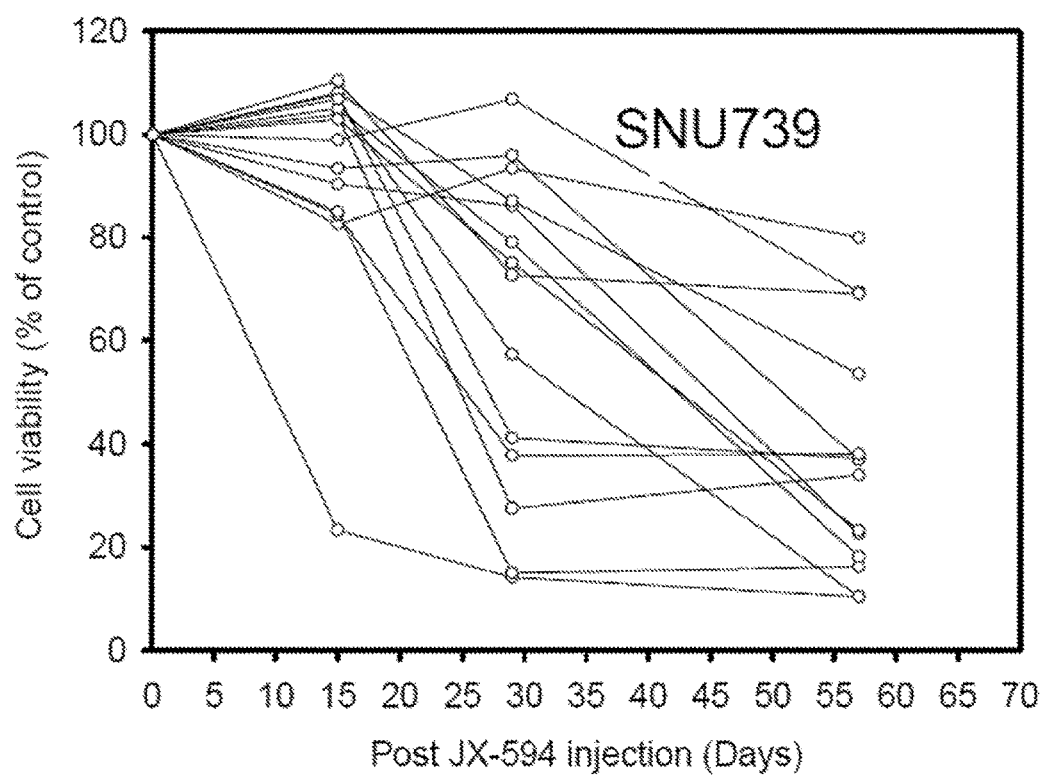
Figure 5D:
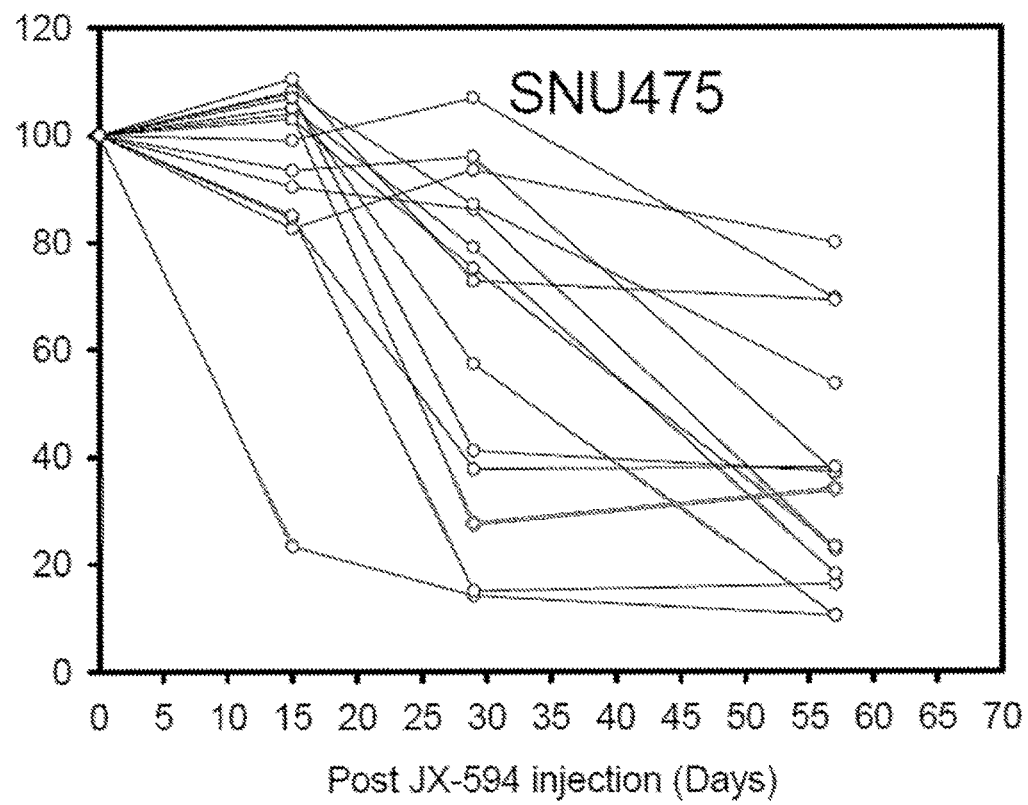
Figure 5E:
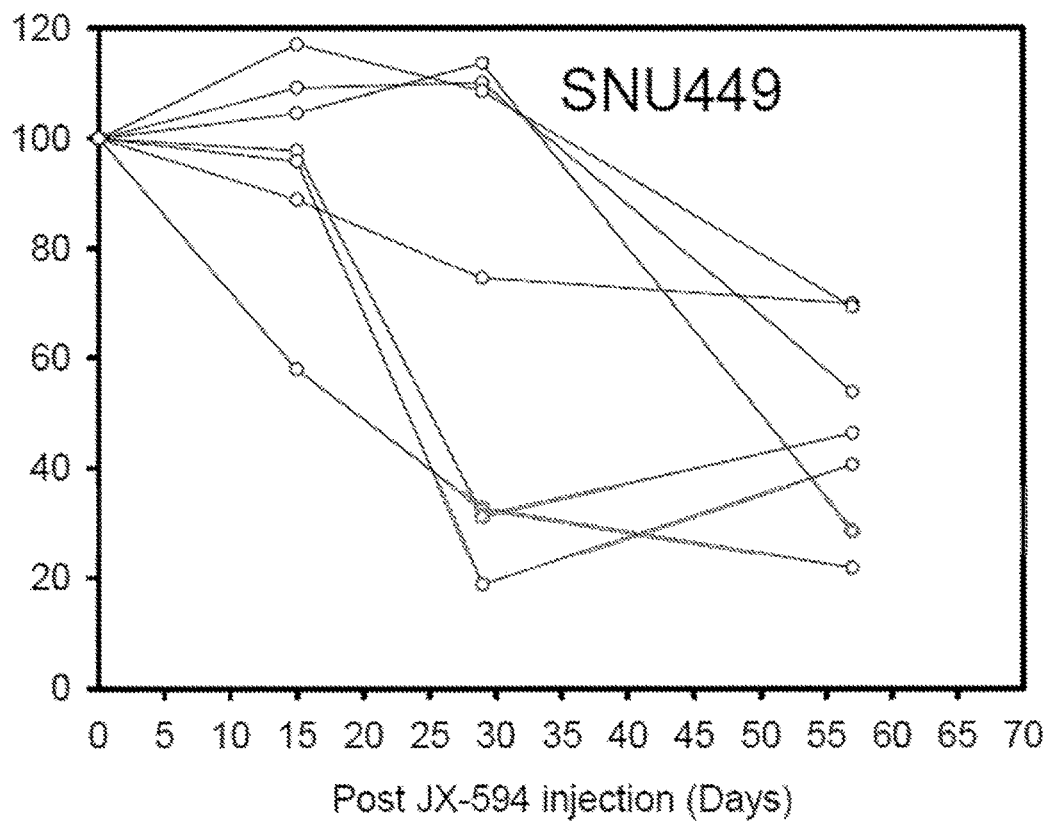

Example 3: Decreased Cell Viability is Due to Antibody-Mediated Complement-Dependent Cytotoxicity We next tested the contribution of antibodies and complement to evaluate the mechanism of by which serum from JX-594 treated patients mediates cancer cell cytotoxicity. Serum from JX-594-treated patients was heat-inactivated to inhibit any complement activity. A column which binds IgG was used to remove antibodies from serum (refer to experimental outline in FIG. 3a). Baseline serum (prior to JX-594 treatment, Serum A), serum obtained 92 days post JX-594 treatment (Serum B), heat-inactivated Serum B (Serum C) and Serum B which was passed through the IgG resin (Serum E) were added to cancer cell line monolayers at a concentration of 5%. Serum collected at baseline did not result in decreased cell viability while serum collected 92 days post JX-594 treatment initiation exhibited potent anti-tumoral activity. However, cells remained viable upon heat-inactivation or IgG depletion. Furthermore, restoration of functional complement in Serum C (by addition of Serum A collected at baseline and not exhibiting decreased cell viability on its own) resulted in restoration of anti-tumoral activity. Similar observations were made with serum samples from a total of three patients treated on the Phase 1 study (301—renal cancer; 103—lung cancer; 304—melanoma) on the cell lines corresponding to the patients' tumor types (FIG. 3b). Bright field images of cell lines post serum incubation (patient 301) are presented in FIG. 3c. Finally, a time-dependent increase in cell viability was observed with respect to the length of heat inactivation (FIG. 3d).

CDC Activity Specific to Tumor Cells and More Effective in Cells of Same Tumor Type.

We next investigated whether serum from JX-594-treated patients was capable of causing toxicity to normal human cells ex vivo. HUVEC endothelial cells and MRC-5 lung fibroblast cells did not exhibit significant decreased cell viability when incubated with serum from any of the five patients tested. Generally, decreased cell viability was observed in cells whose origin corresponded to the patients' tumor type (renal cancer, melanoma and HCC) (FIG. 4a-d). survival versus CDC Phase 1.

CDC Induction Assessed in Randomized Phase 2 Trial

CDC induction was analyzed in HCC patients treated on an ongoing randomized Phase 2 trial. Decreased cell viability was observed in HCC cell lines upon incubation with serum from JX-594-treated patients. CDC activity increased over time (FIG. 4b summary, Figure c-e individual cell lines).

Figure 6:
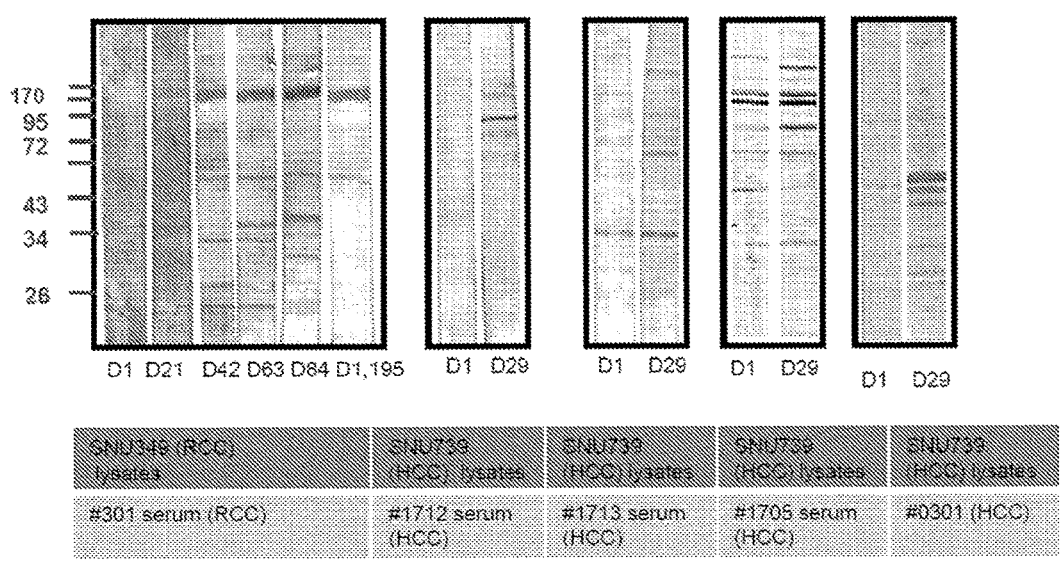
FIG. 6 Western blotting of human serum obtained from JX-594 injected patients.
Figure 7A:
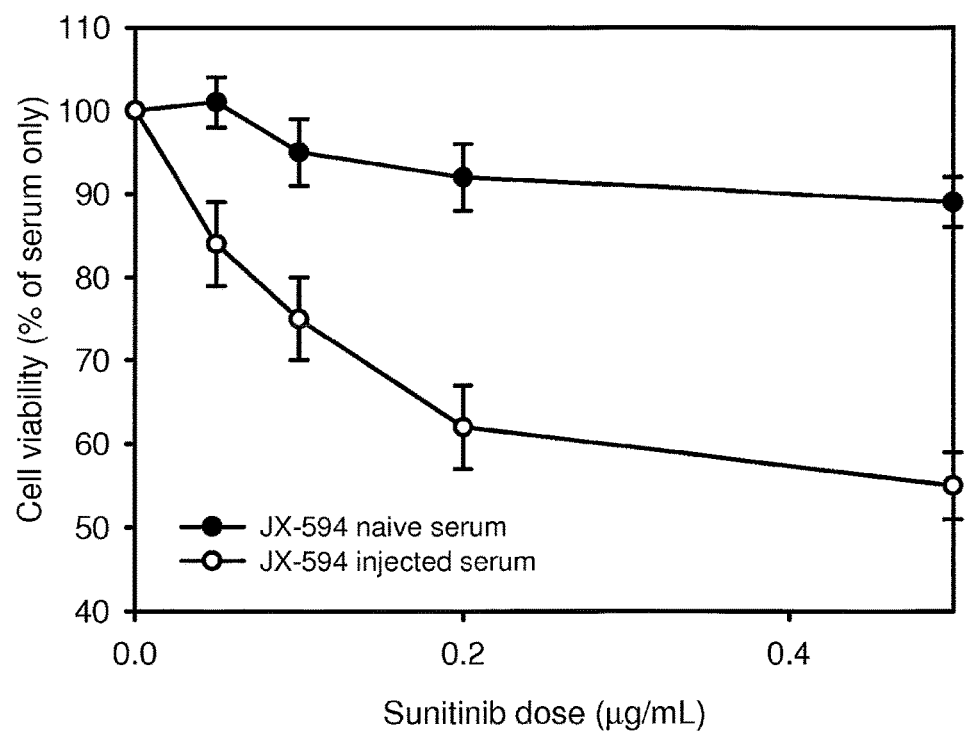
FIGS. 7A-C Sorafenib and sunitinib synergism in vitro (FIGS. 7A and 7B) and in vivo (FIG. 7C) with JX-594 injected serum.
Figure 7B:
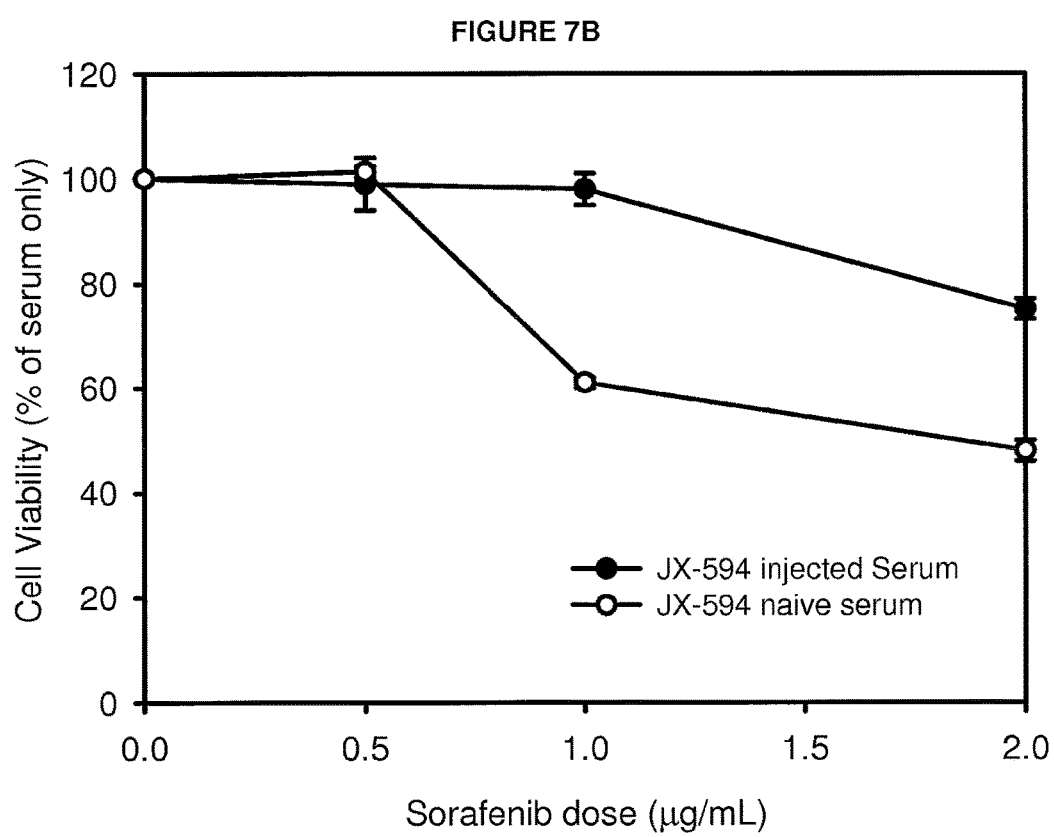
Figure 7C:
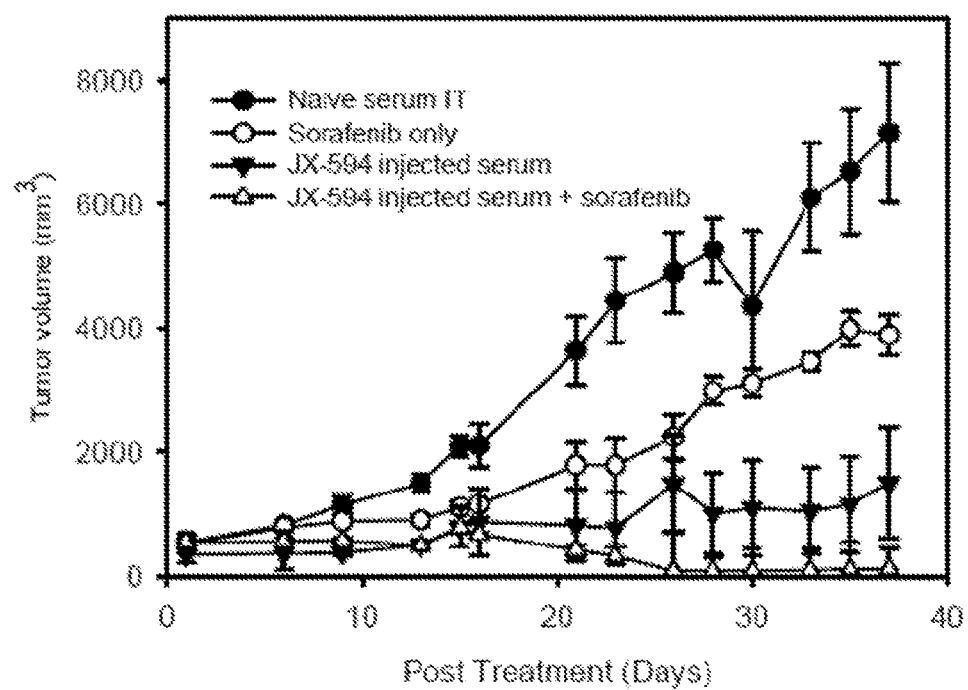
Figure 8:
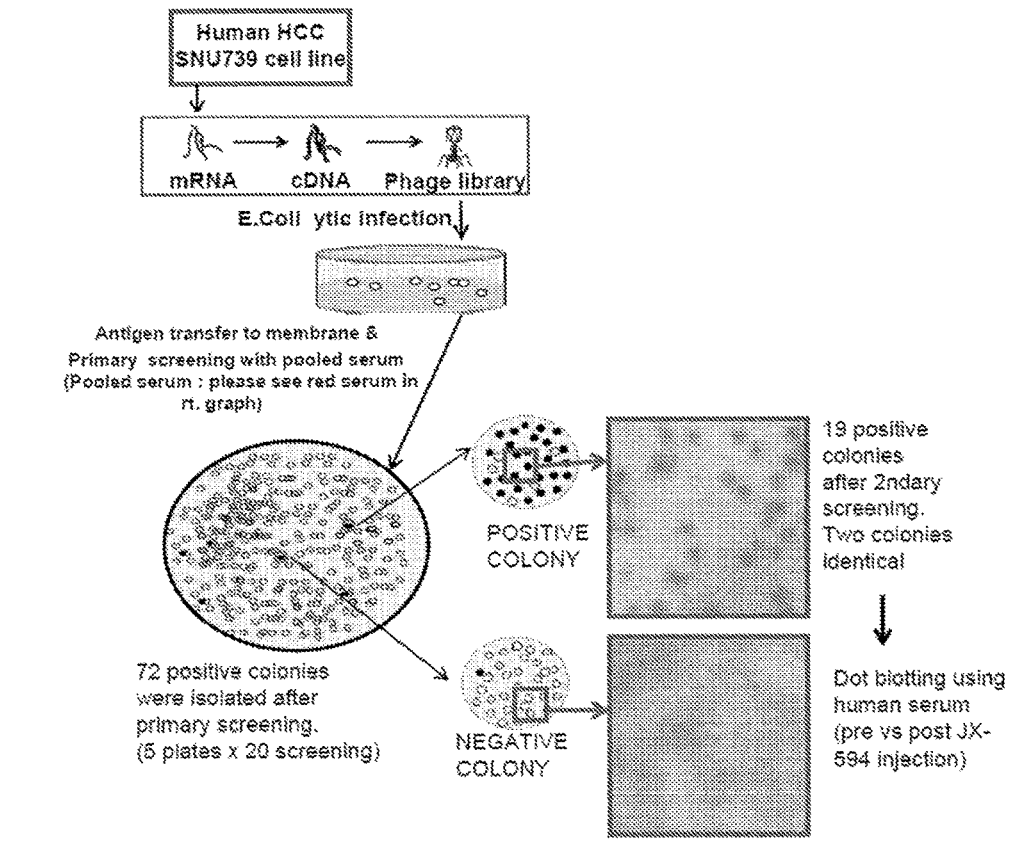
FIG. 8 Method Overview for Serex.

Example 4: SEREX Screening Results in Identification of Endogenous, Novel Tumor Antigens In order to assess whether patient serum binds novel antigens, Western blots were performed using cell lysates from cancer cell lines of the same tissue origin as the patients' tumors and patient serum (from patients on Phase 1 and 2 trials exhibiting significant CDC). Strong reactivity to new antigens was observed in serum after JX-594 treatment, suggestive of induction of polyclonal antibodies to the patients' endogenous tumor antigens (FIG. 6). In order to identify novel target antigens a SEREX screen was performed using serum pooled from patients with HCC with strong CDC activity on a cDNA library generated from a human HCC cell line (SNU449). After two rounds of screening, 17 candidate antigens were identified (FIG. 7, Table 1). A subset of antigens, e.g. RecQ protein-like (DNA helicase Q1-like) (RECQL) and leptin receptor (LEPR) have previously been identified as targets for HCC or other cancers, while others [including ERBB receptor feedback inhibitor 1(ERRFI1), lysosomal protein transmembrane 4 alpha (LAPTM4A) and RAS oncogene family (RAB1B)] are putative HCC antigens and represent potentially novel targets in HCC. Reactivity of patient serum collected prior to JX-594 treatment was tested for reactivity against the 11 identified antigens. Antibodies against a subset of antigens existed prior to JX-594 treatment, however generally reactivity was stronger after JX-594 therapy, suggesting that treatment with a replication-competent poxvirus induces polyclonal antibodies recognizing tumor antigens.

TABLE 1

| Gene name | Interesting note | Comments | References |
|---|---|---|---|
| tubulin, alpha 1c (TUBA1C) | | Increased Levels in Liver Cancer | Biochemistry 2008, 47, 7572-7582 (TUBA1C-increased level) |
| ERBB receptor feedback inhibitor (ERRFI1) | | Mitogen-Inducible Gene 6 (mig6) is a Negative Regulator of Epidermal Growth Factor Receptor Signaling in Hepatocytes and Human Heptocellular Carcinoma (mig6 = erbbfi 1) | Hepatology, 2010 April; 51(4): 1383-90. |
| chromosome 16 open reading frame 61 (C16orf61) | | Breast cancer over expression, function not known | |
| ATPase inhibitory factor 1 (ATPIF1) | | Function not known | |
| stromal antigen 2 (STAG2) | | Transcriptional co-activator | |

TABLE 1-continued

| Gene name | Interesting note | Comments | References |
|---|---|---|---|
| ROD1 regulator of differentiation 1 (ROD1) | Involved in mitogenic activity | Regulator of differentiation 1 (ROD1) binds to amphipathic C-terminal peptide of thrombospondin-4 and is involved in its mitogenic activity | J Cell Phy. 2009 September; 220(3): 672-9 (ROD1-mitogenic activity) |
| leptin receptor LEPR) | Monoclonal Ab against LEPR is being developed as cancer therapeutic drug | Potential role of leptin expression in hepatocellular carcinoma Leptin induces proliferation and anti-apoptosis in human hepatocarcinoma cells by up-regulating cyclin D1 and down-regulating Bax via a Janus kinase 2-linked pathway Leptin Receptor-Related Immune Response in Colorectal Tumors: The Role of Colonocytes and Interleukin-8 | J. Clin Pathol 2006, 59: 930-934 (leptin-hcc) Endocrine-related Cancer (2007) 14; 513-529 (leptin anti-apoptosis) Cancer Res 2008; 68: (22) Nov. 15, 2008 |
| eukaroytic translation elongation factor 1 alpha 1 (EEF1A1) | | The expression levels of the translational factors eEF1a ½ correlate with cell growth but not apoptosis in hepatocellular carcinoma cell lines with different differentiation grade Novel cell death by downregulation of eEF1A1 expression in tetraploids | Biochimie 89 (2007) 1544-1552 (EEF1A1-not apoptosis Cell Death and Differentiation (2009) 16, 139-150 |
| lysosomal protein transmembrane 4 alpha (LAPTM4A) | Membrane Protein | Molecular cloning and characterization of LAPTM4B, a novel gene upregulated in hepatocellular carcinoma Structure analysis and expressions of a novel tetratransmembrane protein, lysosome-associated protein transmembrane 4 beta associated with hepatocellular carcinoma | Oncogene 2003; 22: 5060-5069 (LAPTM4B-tetratransmembrane protein) World J Gastroenterol 2004; 10(11): 1555-1559 (LAPTM4B-upregulated in hcc |
| SIR2L | Function not known | Characterization of a human gene with sequence homology to *Saccharomyces cerevisiae* SIR2 | Gene 234 (1999) 161-168 (SIR2L) |

TABLE 1-continued

| Gene name | Interesting note | Comments | References |
|---|---|---|---|
| RAB1B, RAS oncogene family (RAB1B) | Same gene in 2 independently isolated clones among 15 clones (secondary screening) | Ras oncogene family, HCC high level | www.ncbi.nlm.nih.gov/pubmed/12450215 |
| RecQ protein-like (DNA helicase Q1-like) (RECQL) | siRNA is being developed as anticancer drug RNA sci | Anticancer activity of RecQL1 helicase siRNA in mouse xenograft models RecQL1 DNA repair helicase: A potential tumor marker and therapeutic target against hepatocellular carcinoma | Cancer Sci 2008, 99: 1227-1236 (RecQL1-anticancer activity) |
| nuclear casein kinase and cyclin-dependent kinase substrate 1 (NUCKS1) | Function not known | | |
| APEX nuclease 1 (APEX1) | Genomic instability | S-Adenosylmethionine Regulates Apurinic/Apyrimidinic Endonuclease 1 Stability: Implication in Hepatocarcinogenesis | GASTROENTEROLOGY 2009; 136: 1025-1036 (APEX 1) |
| *Homo sapiens* adenosine A2b receptor (ADORA2B) | Membrane protein | upregulated by hypoxia, Potential Therapeutic target for asthma | J. Exp. Med. (2003) |
| *Homo Sapiens* S100 calcium binding protein A6 (S100A6) | Calcyclin, detected in serum | Function not clear, but probably involved in tumor proliferation, carcinogenesis, increase in Extracellular activity | BBRC, Volume 390, Issue 4, 25 December 2009, Pages 1087-1092 |
| *Homo Sapiens* thymosin beta 4, X-linked (TMSB4X) | | Bad prognostic factor in NSCLS | Oncogene (2003) 22, 8031-8041 NM_021109.3 |
| *Homo Sapiens* CD24 (CD24) | Membrane protein | predictor for poor prognosis in HCC, breast cancer, and ovarian cancer | Clin Cancer Res 2009; 15(17): 5518-27 Clinical Cancer Res 2003 9: 4906 American Journal of Pathology 2002, 161: 1215-1221) |

Example 5: Discussion

The approval of the first immunotherapy for cancer (Provenge, Dendreon, Seattle Wash.) has validated this novel approach to cancer therapy. Autologous dendritic cell populations are exposed to a prostate cancer antigen fused to GM-CSF prior to reinfusion into the patient and this approach has been demonstrated to improve survival of patients with castration-resistant prostate cancer[32]. Non-specific immunostimulatory approaches have also been evaluated as cancer immunotherapy, including treatment with immune-stimulatory cytokines, e.g. IL-2. Many replication-incompetent viral vaccines expressing tumor antigens in the context of immunostimulatory cytokines or co-stimulatory molecules have been evaluated as tumor vaccines. Though effective at inducing a tumor-specific immune response, these strategies have not resulted in significant survival benefit to patients and no viral cancer vaccine has yet been approved by regulatory agencies. Though generalized induction of antibodies to tumor antigens has been observed[9,33], it is unknown whether these antibodies are functional, e.g. whether they mediate CDC.

While oncolytic virus replication and transgene expression have been reproducibly demonstrated in clinical trials, systemic functional anti-cancer immunity induction has not been systematically evaluated on any trial with JX-594 or other oncolytic viruses to date. Generalized induction of CD3+CD4+ and CD3+CD8+ lymphocytes, natural killer cells and various inflammatory cytokines has been demonstrated[26]. In a melanoma clinical trial with HSV-hGM-CSF (Oncovex, Biovex, Cambridge Mass.), phenotypic analysis of T cells derived from tumor samples suggested distinct differences from peripheral blood T cells. Compared to T cells derived from non-treated control patients, there was an increase in melanoma-associated antigen recognized by T cells (MART-1)-specific T cells in tumors undergoing regression after vaccination; functional anti-tumoral immunity was not assessed[28]. Preclinical studies have demonstrated that oncolytic viruses can induce functional cancer-specific immunity, but clinical data has been lacking[24,34-38].

The complement system is comprised of a series of serum proteins which are a part of the innate immune system. The complement system acts in the defense against infection (e.g. by opsonizing or directly lysing invading bacteria) and also forms a link between innate and adaptive immunity[30]. In particular, complement proteins have the potential to lyse cells opsonized by antibodies which were induced in response to a foreign antigen. Indeed, complement-mediated cytotoxicity (CDC) is one of the most potent cell killing systems[30]. CDC activity is harnessed by monoclonal antibodies (mAb) currently used in the treatment of malignancies. The contribution of CDC to the anti-tumoral efficacy of rituximab (a CD20 specific mAb) has been evaluated extensively preclinically[39-41]. Furthermore, involvement of the complement system in rituximab therapy in patients with follicular lymphoma is supported by the observation that patients with a polymorphism in the C1q complement cascade gene had an increased time to progression[42]. Other antibodies have been shown to mediate CDC in cancer cell lines or patient samples, including alemtuzumab for chronic lymphocytic leukemia[43] and panitumumab and cetuximab cancer cell lines of different origins[44]. These observations have led to the development of strategies to improve the inherent CDC activity of tumor-targeted mAbs[45-47] as well as combination therapies with agents that improve CDC activity[48]. However, there is some concern with further enhancement of CDC activity with a therapeutic that is not cancer specific, such as rituximab, as potentiation of cytotoxicity versus normal CD20-expressing PBMCs can be observed[48].

Vaccinia viruses have been shown to be resistant to complement-mediated neutralization in order to facilitate systemic spread of the virus. This is attributed to the inclusion of complement-regulatory proteins within the outside coat of the extracellular-enveloped virus (EEV) form of vaccinia[49]. However, it has been demonstrated that tumor cells infected with vaccinia virus may be more susceptible to complement-mediated neutralization due to depletion of the complement regulatory protein for incorporation into the envelope of released virions[49,50]. Expression of GM-CSF from JX-594-infected cells within the tumor microenvironment may potentiate CDC-mediated killing through stimulation and expansion of NK cells and macrophages[51]. Indeed, JX-594 replication can trigger inflammation within tumors and inflammatory infiltrates have been detected in melanoma lesions treated intratumorally with JX-594[29].

Here we demonstrate the first evidence of induction of functional anti-tumoral immunity in patients treated with an oncolytic virus. JX-594 induces antibody-dependent CDC of tumor cells ex vivo as demonstrated in serum obtained both from tumor-bearing rabbits as well as patients with various advanced, treatment-refractory tumors. The use of replication-competent, oncolytic poxviruses as an anti-cancer immunotherapy has major advantages over other immunotherapeutic strategies: 1) induction of anti-cancer immune responses represent one mechanism-of-action of the therapy; others include direct infection and lysis of tumor cells and acute tumor vascular shutdown; 2) oncolytic poxvirus infection triggers a patient-specific/tailored immune response; 3) no ex vivo manipulation steps are required for the therapy (though effective, the clinically validated Provenge approach is laborious, requiring ex vivo manipulation of each patient's immune cells) and 4) immune stimulation is triggered by active virus infection of tumor cells which triggers an inflammatory reaction within the tumor microenvironment. A major hurdle in the immunotherapy field is for activated immune effector cells to be recruited to and activated within the tumor. Oncolytic poxviruses represent an optimal vehicle by which to stimulate induction of an adaptive immune response while simultaneously triggering induction of pro-inflammatory cytokines and a local inflammatory response within the tumor microenvironment which ensures recruitment and activation of immune cells in the tumor.

The system outlined here represents a mechanism by which novel, patient endogenous tumor antigens can be identified. A SEREX screen identified previously characterized tumor antigens, validating the current approach, as well as novel tumor-associated antigens which represent new potential targets for the treatment of HCC. The experimental design outlined here which involves (1) treatment of a patient with a replication-competent oncolytic poxvirus, (2) measurement of functional anti-tumoral immunity (CDC assay) ex vivo and (3) performing a SEREX screen on patient serum with high CDC activity to identify target antigens, represents a novel approach for the discovery of novel tumor antigens. This method allows for the identification of multiple relevant antigens (patient endogenous antigens able to be recognized by antibodies) to which the generation of antibodies is safe (as the antibodies were generated in humans with no deleterious effects). Here we have demonstrated a proof-of-concept for this method in patients with HCC however this methodology can similarly be used for any other tumor type.

In addition, induction of cytotoxic T lymphocytes to tumor antigens, vaccinia virus as well as the JX-594 transgene β-galactosidase in JX-594 treated patients is currently being evaluated. Effect of combination therapy with anti-angiogenics, including sorafenib (a regimen being tested in Phase 2 trials) on JX-594-induced CDC is being investigated.

Figure 9:
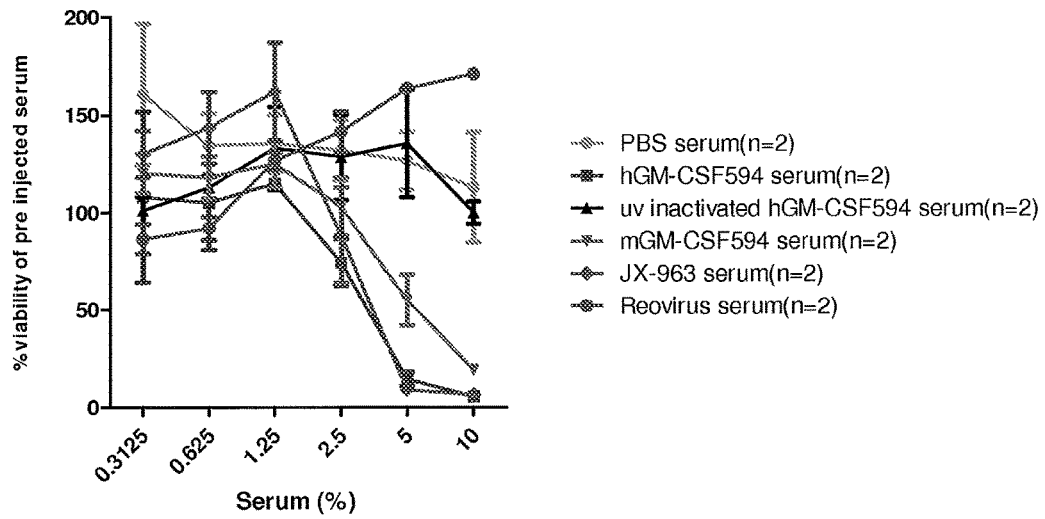
FIG. 9 Oncolytic vaccinia, GM-CSF and reovirus effects on induction of tumor-specific antibodies mediating CDC. This figure shows % A2780 cell viability when compared to pre-treatment control following 3 h incubation with indicated serum concentrations. Serum collected from VX2 tumor-bearing rabbits treated intravenously with the interventions indicated.

Example 6: Oncolytic Vaccinia, GM-CSF and Reovirus Effects on Induction of Tumor-Specific Antibodies Mediating CDC Studies were designed to show that replication-competent oncolytic viruses differentially induce tumor-specific antibodies mediating CDC. Antibody induction can be boosted by expression of immunostimulatory cytokines. In the first of these the effects of oncolytic vaccinia, GM-CSF and reovirus on induction of tumor-specific antibodies mediating CDC response was assessed and the data are shown in FIG. 9.

VX2 tumor-bearing rabbits were treated with two weekly intravenous infusions of PBS, UV inactivated JX-594 expressing human GM-CSF, JX-594 expressing human GM-CSF, JX-594 expressing murine JX-594, JX-963 or reovirus (n=2). Viruses were administered at a dose of $1\times10^9$ pfu. Serum was collected at baseline and 3 weeks post treatment initiation. Rabbit serum was incubated with A2780 cells in vitro at the indicated concentrations for 3 hours. Cell viability relative to viability of A2780 cells incubated with pre-treatment serum was assessed using CCK-8 kit.

From these studies it can be seen that JX-594 expressing human GM-CSF (a cytokine that is biologically active in rabbits) induced CDC starting at a serum concentration of 2.5%. Full CDC activity was reached at 5% serum concentration. Similarly, JX-963 induced CDC at 2.5% serum concentration, with maximal CDC reached at 5% serum concentration. Induction of antibodies mediating CDC was dependent on oncolytic vaccinia replication in rabbits as A2780 incubation with serum collected from rabbits treated with UV inactivated JX-594 expressing human GM-CSF (rendered replication-incompetent) or PBS did not induce CDC at any concentration tested. Similarly, serum collected from rabbits treated with reovirus, an double stranded RNA virus which is currently in clinical development as an oncolytic agent, did not induce CDC at any concentration tested. Finally, treatment with JX-594 expressing murine GM-CSF (which is not as biologically active in rabbits as human GM-CSF) induced CDC only at higher concentrations of serum. These results indicate that expression of the immunostimulatory cytokine GM-CSF may potentiate induction of anti-tumor antibodies mediating CDC.

Figure 10:
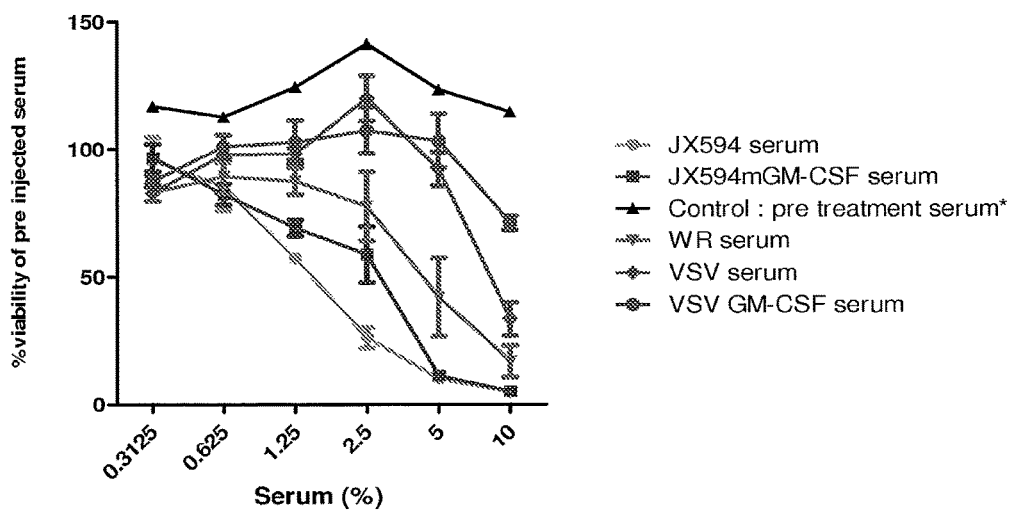
FIG. 10 Oncolytic vaccinia, GM-CSF and VSV effects on induction of tumor-specific antibodies mediating CDC on human cancer cells. This figure shows % A2780 cell viability when compared to pre-treatment control following 3 h incubation with indicated serum concentrations. Serum collected from VX2 tumor-bearing rabbits treated intravenously with the interventions indicated.

Example 7: Oncolytic Vaccinia, GM-CSF and VSV Effects on Induction of Tumor-Specific Antibodies Mediating CDC on Human Cancer Cells In the next set of studies, the effects of oncolytic vaccinia, GM-CSF and VSV on induction of tumor-specific antibodies mediating CDC response was assessed and the data are shown in FIG. 10.

For these experiments, VX2 tumor-bearing rabbits were treated with two weekly intravenous infusions of JX-594 expressing human GM-CSF ($1\times10^9$ pfu), JX-594 expressing murine JX-594 ($1\times10^9$ pfu), Western Reserve vaccinia ($1\times10^9$ pfu), Vesicular Stomatitis Virus (VSV) ($6\times10^8$ pfu) or VSV expressing murine GM-CSF ($6\times10^8$ pfu) (n=2). Serum was collected at baseline and 3 weeks post treatment initiation. Rabbit serum was incubated with A2780 cells in vitro at the indicated concentrations for 3 hours. Cell viability relative to viability of A2780 cells incubated with pre-treatment serum was assessed using CCK-8 kit.

In this experiment, JX-594 expressing human GM-CSF (JX-594) was most efficient at inducing CDC mediating antibodies, with a decrease in cell viability apparent upon incubation with 1.25% and 2.5% serum. In contrast, treatment with JX-594 expressing murine GM-CSF (which is not as biologically active in rabbits as human GM-CSF) induced CDC only at higher concentrations of serum (note: as an additional control, VSV expressing murine GM-CSF did not induce CDC at any concentration tested). Furthermore, treatment of rabbits with the wild-type western reserve strain of vaccinia (which does not encode GM-CSF) was less efficient at inducing antibodies mediating CDC. Finally treatment with the single-stranded negative sense RNA virus VSV induced CDC-mediating antibodies only at the highest serum concentration tested (10%). These results suggest that depending on oncolytic virus biology, different levels of CDC response can be observed.

Figure 11:
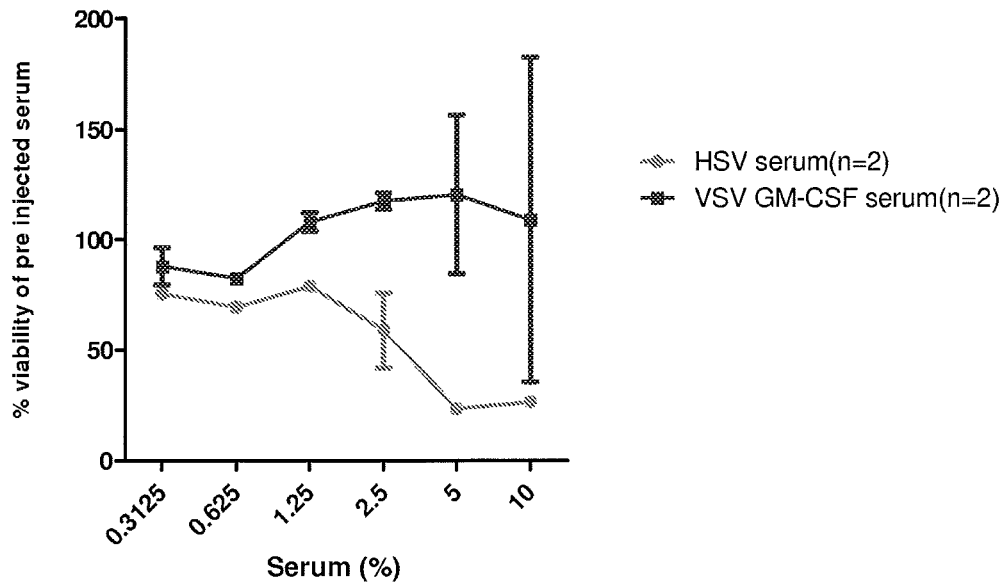
FIG. 11 Oncolytic HSV and VSV-GM-CSF effects on induction of tumor-specific antibodies mediating CDC on human cancer cells. This figure shows % A2780 cell viability when compared to pre-treatment control following 3 h incubation with indicated serum concentrations. Serum collected from VX2 tumor-bearing rabbits treated intravenously with the interventions indicated.

Example 8: Oncolvtic HSV and VSV-GM-CSF Effects on Induction of Tumor-Specific Antibodies Mediating CDC on Human Cancer Cells In this set of experiments, the oncolytic HSV and VSV-GM-CSF on induction of tumor-specific antibodies mediating CDC on human cancer cells was assessed and the data are shown in FIG. 11.

VX2 tumor-bearing rabbits were treated with two weekly intravenous infusions of VSV expressing murine GM-CSF ($6\times10^8$ pfu) or Herpes Simplex Virus (HSV) ($1\times10^9$ pfu) (n=2). Serum was collected at baseline and 3 weeks post treatment initiation. Rabbit serum was incubated with A2780 cells in vitro at the indicated concentrations for 3 hours. Cell viability relative to viability of A2780 cells incubated with pre-treatment serum was assessed using CCK-8 kit.

In this experiment, HSV was most efficient at inducing CDC mediating antibodies, with a decrease in cell viability apparent upon incubation with 5% and 10% serum. VSV expressing GM-CSF did not induce CDC in this experiment (though high variability was observed at the 10% serum condition).

Figure 12:
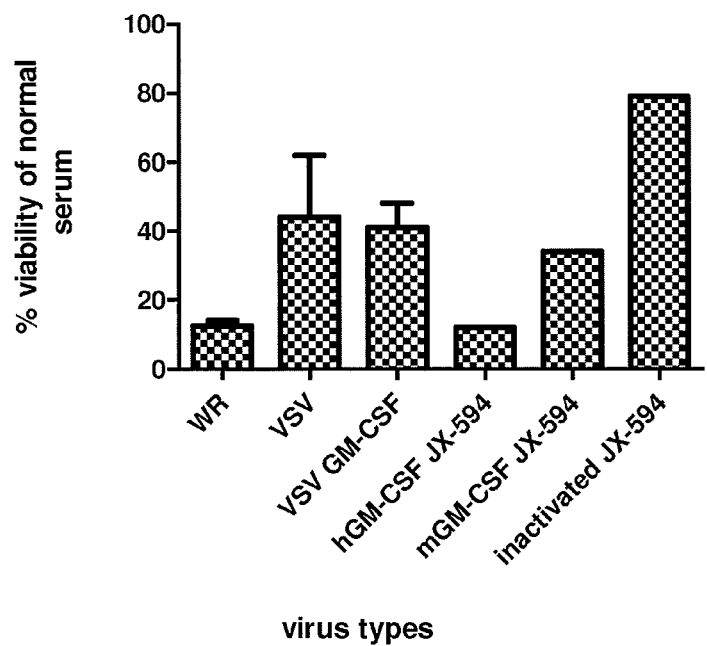
FIG. 12 Oncolytic vaccinia, GM-CSF and VSV effects on induction of tumor-specific antibodies mediating CDC on rabbit cancer cells derived from the in vivo target tumor. This figure shows % VX2 cell viability when compared to pre-treatment control following 24 h incubation with 3% post-treatment serum spiked with 7% serum collected before VX2 implantation. Serum collected from VX2 tumor-bearing rabbits treated intravenously with the oncolytic viruses is indicated on the x axis.

Example 9: Oncolvtic Vaccinia, GM-CSF and VSV Effects on Induction of Tumor-Specific Antibodies Mediating CDC on Rabbit Cancer Cells Derived from the In Vivo Target Tumor In this set of experiments, the effects of oncolytic vaccinia, GM-CSF and VSV on induction of tumor-specific antibodies mediating CDC on rabbit cancer cells from an in vivo target tumor were assessed and the data are shown in FIG. 12.

VX2 tumor-bearing rabbits were treated with two weekly intravenous infusions of JX-594 expressing human GM-CSF ($1\times10^9$ pfu), JX-594 expressing murine JX-594 ($1\times10^9$ pfu), Western Reserve vaccinia ($1\times10^9$ pfu), Vesicular Stomatitis Virus (VSV) ($6\times10^8$ pfu) or VSV expressing murine GM-CSF ($6\times10^8$ pfu) or UV inactivated JX-594 expressing human GM-CSF (n=2). Serum was collected at baseline and 3 weeks post treatment initiation. Rabbit serum was incubated with VX2 cells in vitro for 24 hours. Cell viability relative to viability of VX2 cells incubated with pre-treatment serum was assessed using CCK-8 kit.

In order to induce CDC on VX2 target cells, additional complement contained in serum collected prior to oncolytic virus administration was spiked into 3% post-treatment serum. As in prior experiments, UV inactivated JX-594 was not able to induce antibodies mediating CDC in this setting. JX-594 expressing human GM-CSF, JX-594 expressing murine GM-CSF and western reserve vaccinia all induced CDC in this assay, supporting the ability of replication-competent vaccinia viruses to induce anti-tumor antibodies mediating CDC (in this setting the target cells were derived from the tumor against which antibodies were raised in the oncolytic virus treated rabbits). VSV (+/−murine GM-CSF) was not as efficient as inducing anti-tumor antibodies as any of the oncolytic vaccinia viruses tested.

Figure 13:
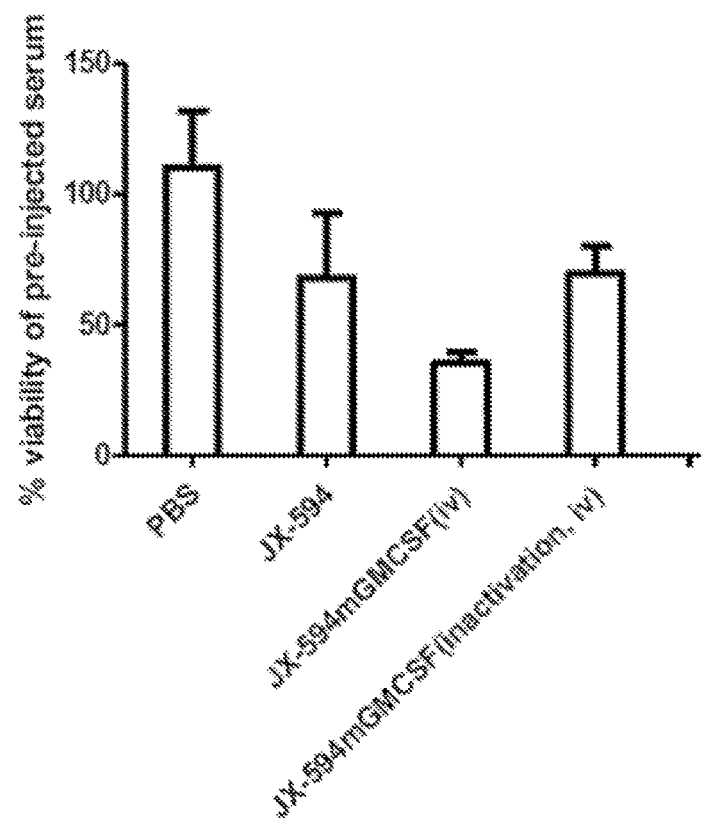
FIG. 13 Oncolytic vaccinia and murine GM-CSF expression mediate induction of tumor-specific antibodies mediating CDC in a murine tumor model. This figure shows % A2780 cell viability when compared to pre-treatment control following 24 h incubation with 5% post-treatment serum. Serum collected from CT26 tumor-bearing mice treated intravenously with the oncolytic viruses is indicated on the x axis.

Example 10: Oncolytic Vaccinia and Murine GM-CSF Expression Mediate Induction of Tumor-Specific Antibodies Mediating CDC in a Murine Tumor Model In this example, the effects of oncolytic vaccinia, and murine GM-CSF mediated induction of tumor-specific antibodies mediating CDC on murine tumor model were assessed and the data are shown in FIG. 13.

CT26 tumor-bearing mice were treated with four weekly intravenous infusions of JX-594 expressing human GM-CSF, JX-594 expressing murine JX-594, PBS or UV inactivated JX-594 expressing human GM-CSF (n=3). Viruses were administered at a dose of $1\times10^7$ pfu. Serum was collected at baseline and 4 weeks post treatment initiation. Mouse serum was incubated with A2780 cells in vitro for 24 hours. Cell viability relative to viability of A2780 cells incubated with pre-treatment serum was assessed using CCK-8 kit.

CDC experiments were repeated in a syngeneic mouse model (Balb/C mice bearing subcutaneous CT26 tumors). JX-594 expressing murine GM-CSF was most potent at inducing anti-tumor antibodies mediating CDC. Both JX-594 expressing human GM-CSF (JX-594; human GM-CSF is known not to be active in rodents) as well as UV-inactivated JX-594 expressing murine GM-CSF had an intermediate effect on CDC induction (when comparing to PBS and JX-594 expressing murine GM-CSF). This may indicate that in this mouse model both replication as well as high-level murine GM-CSF expression (which only occurs upon treatment with the replication-competent vaccinia backbone) is necessary to induce high-titer anti-tumor antibodies that mediate CDC in vitro.

REFERENCES CITED

1. Petrelli A, Giordano S. From single- to multi-target drugs in cancer therapy: when aspecificity becomes an advantage. Curr Med Chem. 2008; 15(5):422-32.
2. Podar K, Tonon G, Sattler M, Tai Y T, Legouill S, Yasui H, et al. The small-molecule VEGF receptor inhibitor pazopanib (GW786034B) targets both tumor and endothelial cells in multiple myeloma. Proc Natl Acad Sci USA. 2006 Dec. 19; 103(51):19478-83.
3. Demetri G D, van Oosterom A T, Garrett C R, Blackstein M E, Shah M H, Verweij J, et al. Efficacy and safety of sunitinib in patients with advanced gastrointestinal stromal tumour after failure of imatinib: a randomised controlled trial. Lancet. 2006 Oct. 14; 368(9544):1329-38.
4. Le Tourneau C, Faivre S, Raymond E. New developments in multitargeted therapy for patients with solid tumours. Cancer Treat Rev. 2008 February; 34(1):37-48.
5. Kerr D. Clinical development of gene therapy for colorectal cancer. Nat Rev Cancer. 2003 August; 3(8):615-22.
6. Zeimet A G, Marth C. Why did p53 gene therapy fail in ovarian cancer? Lancet Oncol. 2003 July; 4(7):415-22.
7. McCormick F. Cancer gene therapy: fringe or cutting edge? Nat Rev Cancer. 2001 November; 1(2):130-41.
8. Rosenberg S A, Yang J C, Restifo N P. Cancer immunotherapy: moving beyond current vaccines. Nat Med. 2004 September; 10(9):909-15.
9. Amato R J, Drury N, Naylor S, Jac J, Saxena S, Cao A, et al. Vaccination of prostate cancer patients with modified vaccinia ankara delivering the tumor antigen 5T4 (TroVax): a phase 2 trial. J Immunother. 2008 July-August; 31(6):577-85.
10. Gulley J L, Arlen P M, Tsang K Y, Yokokawa J, Palena C, Poole D J, et al. Pilot study of vaccination with recombinant CEA-MUC-1-TRICOM poxviral-based vaccines in patients with metastatic carcinoma. Clin Cancer Res. 2008 May 15; 14(10):3060-9.
11. Heise C, Sampson-Johannes A, Williams A, McCormick F, Von Hoff D D, Kirn D H. ONYX-015, an E1B gene-attenuated adenovirus, causes tumor-specific cytolysis and antitumoral efficacy that can be augmented by standard chemotherapeutic agents. Nat Med. 1997 June; 3(6):639-45.
12. Bell J C, Lichty B, Stojdl D. Getting oncolytic virus therapies off the ground. Cancer Cell. 2003 July; 4(1):7-11.
13. Parato K A, Senger D, Forsyth P A, Bell J C. Recent progress in the battle between oncolytic viruses and tumours. Nat Rev Cancer. 2005 December; 5(12):965-76.
14. Thorne S H, Hermiston T, Kirn D. Oncolytic virotherapy: approaches to tumor targeting and enhancing antitumor effects. Semin Oncol. 2005 December; 32(6):537-48.
15. Coffey M C, Strong J E, Forsyth P A, Lee P W. Reovirus therapy of tumors with activated Ras pathway. Science. 1998 Nov. 13; 282(5392):1332-4.
16. Norman K L, Lee P W. Reovirus as a novel oncolytic agent. J Clin Invest. 2000 April; 105(8):1035-8.
17. Stojdl D F, Lichty B, Knowles S, Marius R, Atkins H, Sonenberg N, et al. Exploiting tumor-specific defects in the interferon pathway with a previously unknown oncolytic virus. Nat Med. 2000 July; 6(7):821-5.
18. Stojdl D F, Lichty B D, tenOever B R, Paterson J M, Power A T, Knowles S, et al. VSV strains with defects in their ability to shutdown innate immunity are potent systemic anti-cancer agents. Cancer Cell. 2003 October; 4(4): 263-75.
19. Bischoff J R, Kirn D H, Williams A, Heise C, Horn S, Muna M, et al. An adenovirus mutant that replicates selectively in p53-deficient human tumor cells. Science. 1996 Oct. 18; 274(5286):373-6.
20. Heise C, Hermiston T, Johnson L, Brooks G, Sampson-Johannes A, Williams A, et al. An adenovirus E1A mutant that demonstrates potent and selective antitumoral efficacy. Nature Medicine. 2000; 6(10):1134-9.
21. Mineta T, Rabkin S D, Yazaki T, Hunter W D, Martuza R L. Attenuated multi-mutated herpes simplex virus-1 for the treatment of malignant gliomas. Nat Med. 1995 September; 1(9):938-43.
22. Mineta T, Rabkin S D, Martuza R L. Treatment of malignant gliomas using ganciclovir-hypersensitive, ribonucleotide reductase-deficient herpes simplex viral mutant. Cancer Res. 1994 Aug. 1; 54(15):3963-6.
23. Liu T C, Hwang T H, Bell J C, Kirn D H. Translation of targeted oncolytic virotherapeutics from the lab into the clinic, and back again: a high-value iterative loop. Mol Ther. 2008 June; 16(6):1006-8.
24. Kim J H, Oh J Y, Park B H, Lee D E, Kim J S, Park H E, et al. Systemic armed oncolytic and immunologic therapy for cancer with JX-594, a targeted poxvirus expressing GM-CSF. Mol Ther. 2006 September; 14(3):361-70.
25. Payne L G. Significance of extracellular enveloped virus in the in vitro and in vivo dissemination of vaccinia. J Gen Virol. 1980 September; 50(1):89-100.
26. Park B H, Hwang T, Liu T C, Sze D Y, Kim J S, Kwon H C, et al. Use of a targeted oncolytic poxvirus, JX-594, in patients with refractory primary or metastatic liver cancer: a phase I trial. Lancet Oncol. 2008 June; 9(6):533-42.
27. Senzer N N, Kaufman H L, Amatruda T, Nemunaitis M, Reid T, Daniels G, et al. Phase II clinical trial of a granulocyte-macrophage colony-stimulating factor-encoding, second-generation oncolytic herpesvirus in patients with unresectable metastatic melanoma. J Clin Oncol. 2009 Dec. 1; 27(34):5763-71.
28. Kaufman H L, Kim D W, DeRaffele G, Mitcham J, Coffin R S, Kim-Schulze S. Local and distant immunity induced by intralesional vaccination with an oncolytic herpes virus encoding GM-CSF in patients with stage IIIc and IV melanoma. Ann Surg Oncol. 2010 March; 17(3):718-30.

29. Mastrangelo M J, Maguire H C, Jr., Eisenlohr L C, Laughlin C E, Monken C E, McCue P A, et al. Intratumoral recombinant GM-CSF-encoding virus as gene therapy in patients with cutaneous melanoma. Cancer Gene Ther. 1999 September-October; 6(5):409-22.

30. Walport M J. Complement. First of two parts. N Engl J Med. 2001 Apr. 5; 344(14):1058-66.

31. Lee J H, Roh M S, Lee Y K, Kim M K, Han J Y, Park B H, et al. Oncolytic and immunostimulatory efficacy of a targeted oncolytic poxvirus expressing human GM-CSF following intravenous administration in a rabbit tumor model. Cancer Gene Ther. 2010 February; 17(2):73-9.

32. Higano C S, Schellhammer P F, Small E J, Burch P A, Nemunaitis J, Yuh L, et al. Integrated data from 2 randomized, double-blind, placebo-controlled, phase 3 trials of active cellular immunotherapy with sipuleucel-T in advanced prostate cancer. Cancer. 2009 Aug. 15; 115(16): 3670-9.

33. Amato R J, Shingler W, Naylor S, Jac J, Willis J, Saxena S, et al. Vaccination of renal cell cancer patients with modified vaccinia ankara delivering tumor antigen 5T4 (TroVax) administered with interleukin 2: a phase II trial. Clin Cancer Res. 2008 Nov. 15; 14(22):7504-10.

34. Aigner F, Conrad F, Widschwendter A, Zangerle R, Zelger B, Haidenberger A, et al. [Anal HPV infections]. Wien Klin Wochenschr. 2008; 120(19-20):631-41.

35. Prestwich R J, Ilett E J, Errington F, Diaz R M, Steele L P, Kottke T, et al. Immune-mediated antitumor activity of reovirus is required for therapy and is independent of direct viral oncolysis and replication. Clin Cancer Res. 2009 Jul. 1; 15(13):4374-81.

36. Li H, Dutuor A, Fu X, Zhang X. Induction of strong antitumor immunity by an HSV-2-based oncolytic virus in a murine mammary tumor model. J Gene Med. 2007 March; 9(3):161-9.

37. Li Q X, Liu G, Wong-Staal F. Oncolytic virotherapy as a personalized cancer vaccine. Int J Cancer. 2008 Aug. 1; 123(3):493-9.

38. Parato K A, Lichty B D, Bell J C. Diplomatic immunity: turning a foe into an ally. Curr Opin Mol Ther. 2009 February; 11(1):13-21.

39. Harjunpaa A, Junnikkala S, Meri S. Rituximab (anti-CD20) therapy of B-cell lymphomas: direct complement killing is superior to cellular effector mechanisms. Scand J Immunol. 2000 June; 51(6):634-41.

40. Di Gaetano N, Cittera E, Nota R, Vecchi A, Grieco V, Scanziani E, et al. Complement activation determines the therapeutic activity of rituximab in vivo. J Immunol. 2003 Aug. 1; 171(3):1581-7.

41. Golay J, Cittera E, Di Gaetano N, Manganini M, Mosca M, Nebuloni M, et al. The role of complement in the therapeutic activity of rituximab in a murine B lymphoma model homing in lymph nodes. Haematologica. 2006 February; 91(2):176-83.

42. Racila E, Link B K, Weng W K, Witzig T E, Ansell S, Maurer M J, et al. A polymorphism in the complement component C1qA correlates with prolonged response following rituximab therapy of follicular lymphoma. Clin Cancer Res. 2008 Oct. 15; 14(20):6697-703.

43. Zent C S, Secreto C R, LaPlant B R, Bone N D, Call T G, Shanafelt T D, et al. Direct and complement dependent cytotoxicity in CLL cells from patients with high-risk early-intermediate stage chronic lymphocytic leukemia (CLL) treated with alemtuzumab and rituximab. Leuk Res. 2008 December; 32(12):1849-56.

44. Dechant M, Weisner W, Berger S, Peipp M, Beyer T, Schneider-Merck T, et al. Complement-dependent tumor cell lysis triggered by combinations of epidermal growth factor receptor antibodies. Cancer Res. 2008 Jul. 1; 68(13): 4998-5003.

45. Weiner L M, Surana R, Wang S. Monoclonal antibodies: versatile platforms for cancer immunotherapy. Nat Rev Immunol. 2010 May; 10(5):317-27.

46. Morris J C, Waldmann T A. Antibody-based therapy of leukaemia. Expert Rev Mol Med. 2009; 11:e29.

47. Coiffier B, Lepretre S, Pedersen L M, Gadeberg O, Fredriksen H, van Oers M H, et al. Safety and efficacy of ofatumumab, a fully human monoclonal anti-CD20 antibody, in patients with relapsed or refractory B-cell chronic lymphocytic leukemia: a phase 1-2 study. Blood. 2008 Feb. 1; 111(3):1094-100.

48. Wang H, Liu Y, Li Z Y, Fan X, Hemminki A, Lieber A. A recombinant adenovirus type 35 fiber knob protein sensitizes lymphoma cells to rituximab therapy. Blood. 2010 Jan. 21; 115(3):592-600.

49. Vanderplasschen A, Mathew E, Hollinshead M, Sim R B, Smith G L. Extracellular enveloped vaccinia virus is resistant to complement because of incorporation of host complement control proteins into its envelope. Proc Natl Acad Sci USA. 1998 Jun. 23; 95(13):7544-9.

50. Baranyi L, Okada N, Baranji K, Takizawa H, Okada H. Membrane-bound complement regulatory activity is decreased on vaccinia virus-infected cells. Clin Exp Immunol. 1994 October; 98(1):134-9.

51. Liu Z, Lee F T, Hanai N, Smyth F E, Burgess A W, Old L J, et al. Cytokine enhancement of in vitro antibody-dependent cellular cytotoxicity mediated by chimeric anti-GD3 monoclonal antibody KM871. Cancer Immun. 2002 Oct. 7; 2:13.

52. Kirn D H, Wang Y, Le Boeuf F, Bell J, Thorne S H. Targeting of interferon-beta to produce a specific, multi-mechanistic oncolytic vaccinia virus. PLoS Med. 2007 December; 4(12):e353.

53. Thorne S H, Hwang T H, O'Gorman W E, Bartlett D L, Sei S, Kanji F, et al. Rational strain selection and engineering creates a broad-spectrum, systemically effective oncolytic poxvirus, JX-963. J Clin Invest. 2007 Nov. 1; 117(11):3350-8.

54. McCart J A, Ward J M, Lee J, Hu Y, Alexander H R, Libutti S K, et al. Systemic cancer therapy with a tumor-selective vaccinia virus mutant lacking thymidine kinase and vaccinia growth factor genes. Cancer Res. 2001 Dec. 15; 61(24):8751-7.

55. Guo Z S, Naik A, O'Malley M E, Popovic P, Demarco R, Hu Y, et al. The enhanced tumor selectivity of an oncolytic vaccinia lacking the host range and antiapoptosis genes SPI-1 and SPI-2. Cancer Res. 2005 Nov. 1; 65(21): 9991-8.

56. Liu T C, Hwang T, Park B H, Bell J, Kirn D H. The targeted oncolytic poxvirus JX-594 demonstrates antitumoral, antivascular, and anti-HBV activities in patients with hepatocellular carcinoma. Mol Ther. 2008 September; 16(9):1637-42.

The invention claimed is:
1. A method of identifying a tumor-specific antigen comprising
   a) contacting (i) a plurality of expression vectors into which a cDNA library prepared from a cancer cell has been cloned with (ii) serum isolated from one or more human subjects having a tumor, said one or more subjects having been administered a replication competent oncolytic Wyeth or Western Reserve strain vaccinia virus in an amount effective to mediate a comple- ment dependent cytotoxic (CDC) response specific to said tumor in the subject prior to isolating said serum; and b) isolating antigens from said cDNA library that are recognized by the serum, wherein the method further comprises confirming the presence of CDC response-producing antibodies in said serum after the replication competent oncolytic virus has been administered and before contacting said serum with said plurality of expression vectors.

2. The method of claim 1, wherein said antigens are recognized by polyclonal antibodies induced by treatment with said replication competent oncolytic virus.

3. The method of claim 2, wherein said antigens are not recognized by serum from a human subject with the same tumor type that has not been administered said replication competent oncolytic virus.

4. The method of claim 1, further comprising the step of cloning the cDNA library prepared from the cancer cell into expression vector(s).

5. The method of claim 1, further comprising the step of isolating serum from blood collected from the subject to which the oncolytic virus has been administered.

6. The method of claim 1, wherein the tumor and cancer cell are the same cancer type.

7. The method of claim 1, wherein said serum comprises pooled serum from a plurality of human subjects with the same tumor type that have been administered said replication competent oncolytic virus.

8. The method of claim 1, wherein the tumor is selected from astrocytoma, oligodendroglioma, meningioma, neurofibroma, glioblastoma, ependymoma, Schwannoma, neurofibrosarcoma, neuroblastoma, pituitary adenoma, medulloblastoma, head and neck cancer, melanoma, prostate carcinoma, renal cell carcinoma, pancreatic cancer, breast cancer, lung cancer, colon cancer, bladder cancer, liver cancer, bone cancer, rectal cancer, ovarian cancer, sarcoma, esophageal cancer, stomach cancer, cervical cancer, fibrosarcoma, squamous cell carcinoma, neurectodermal, thyroid tumor, Hodgkin's lymphoma, non-Hodgkin's lymphoma, malignant hepatoma, mesothelioma, epidermoid carcinoma, and tumorigenic diseases of the blood.

9. The method of claim 8, wherein the tumor is selected from colon cancer, rectal cancer, hepatocellular carcinoma, renal cell carcinoma, bladder cancer, lung cancer, stomach cancer, pancreatic cancer, melanoma, ovarian cancer, head and neck cancer, esophageal cancer, sarcoma and mesothelioma.

10. The method of claim 1, wherein the replication competent oncolytic Wyeth or Western Reserve strain vaccinia virus comprises a transgene.

11. The method of claim 1, wherein the transgene comprises a heterologous nucleic acid sequence encoding GM-CSF, cytosine deaminase, or carboxyl esterase.

12. The method of claim 10, wherein the heterologous nucleic acid sequence encodes GM-CSF.

13. The method of claim 11, wherein the oncolytic vaccinia virus is JX-594.

* * * * *